(12) United States Patent
Palhan et al.

(10) Patent No.: US 6,485,937 B1
(45) Date of Patent: Nov. 26, 2002

(54) SYSTEM FOR RAPID GENERATION OF RECOMBINANT BACULOVIRUS-BASED EXPRESSION VECTORS FOR SILKWORM LARVAE

(75) Inventors: Vikas B. Palhan, New York, NY (US); Robert G. Roeder, New York, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 09/690,146

(22) Filed: Oct. 16, 2000

Related U.S. Application Data
(60) Provisional application No. 60/159,707, filed on Oct. 15, 1999.

(51) Int. Cl.[7] .............................. C12P 21/06; C12N 5/06
(52) U.S. Cl. ...................... 435/69.1; 435/71.1; 435/348
(58) Field of Search ................................ 435/69.1, 71.1, 435/348

(56) References Cited

U.S. PATENT DOCUMENTS

| | | | |
|---|---|---|---|
| 4,745,051 A | 5/1988 | Smith et al. | 435/68 |
| 5,023,328 A | 6/1991 | Summers et al. | 536/27 |
| 5,110,729 A | 5/1992 | Maeda et al. | 435/69.1 |
| 5,155,037 A | 10/1992 | Summers | 435/240.2 |
| 5,278,050 A | 1/1994 | Summers | 435/69.1 |
| 5,521,081 A | 5/1996 | Inaoka et al. | 435/212 |
| 5,674,485 A | 10/1997 | Hammock et al. | 424/93.2 |
| 5,714,314 A | 2/1998 | Miyamura et al. | 435/5 |
| 5,734,019 A | 3/1998 | Miyamura et al. | 530/350 |
| 5,750,383 A | 5/1998 | Blissard et al. | 435/172.3 |
| 5,772,586 A | 6/1998 | Heinonen et al. | 600/300 |
| 5,843,883 A | 12/1998 | Gospodarowicz et al. | 514/2 |
| 5,863,767 A | 1/1999 | Gospodarowicz et al. | 435/694 |

OTHER PUBLICATIONS

Choudary et al., Methods in Molecular Biology 1995; 39:243–264.
Palhan et al., Biotechniques, "Baculovirus Mediated High–Level Expression of Luciferase in Silkworm Cells and Larvae", 1995; 19(1):97–104.
Gomi et al., Journal of General Virology 1999; 80:1323–1337.
Johnson et al., Biotechnology and Bioengineering 1993; 42:1293–1300.
Kaduno–Okuda et al., Biochem Biophys Res Commun 1995; 213(2):389–96.
Kitts et al., Nucleic Acids Res. 1990; 18: 5667–5672.
Kitts and Possee, Biotechniques 1993; 5:810–817.
Luckow et al., J. Virol. 1993; 67: 4566–4579.
Maeda, Ann Rev. Entomol. 1989; 34:351–372.
Maeda et al., Nature 1985; 315(6020):592–4.
Matsuoka et al., Vaccine Feb. 1996;14(2):120–6.
Morishita et al., J Biochem (Tokyo) Jan. 1991;109(1):36–44.
Nyunoya et al., AIDS Res Hum Retroviruses Nov. 1990;6(11):1311–21.

(List continued on next page.)

Primary Examiner—Hankyel T. Park
Assistant Examiner—Stacy S. Brown
(74) Attorney, Agent, or Firm—Darby & Darby

(57) ABSTRACT

Recombinant expression systems for the production of proteins, and particularly a system for rapidly generating recombinant silkworm baculoviruses. *Bombyx mori* nuclear polyhedrosis virus (BmNPV) with an efficiency approaching 100% has been developed. In a specific example, the vector of the invention was used to generate expression of a FLAG-epitope tagged HIV tat interacting protein of 30 kDa (f-TIP30) in BmN cells and silkworm larvae.

32 Claims, 17 Drawing Sheets

OTHER PUBLICATIONS

Palhan et al., Current Science 1996; 70(2):147–153.
Patel et al., Nucleic Acids Res. 1992; 20:97–104.
Peakman et al., Nucleic Acids Res. 1989; 17:5403.
Peakman et al., Nucleic Acids Res. 1992; 20: 495–500.
Sriram et al., Gene 1997; 190:181–169.
Vialard et al., J. Virol. 1990; 64: 37–50.
Vlak et al., Virol. 1990; 179: 312–320.
Weyer et al., J. Gen. Virol. 1990; 71: 1525–1534.
Xiao et al., The EMBO J. 2000; 19(5):956–961.
Zuidema et al., J. Gen. Virol. 1990; 71: 2201–2209.
Deng et al., Chin J Biotechnol 1995;11(2):109–17.
Francki, R. I. B., et al., eds., in Archives of Virology, (1991), Supp. 2, pp. 117–123.
Higashihashi et al., J. Virol. Methods Nov.–Dec. 1991;35(2):159–67.
MiyaJima et al., Gene 1987;58(2–3):273–81.
Mori et al., Avian Dis Oct.–Dec. 1994;38(4):772–7.
Morishita et al., Jpn J Cancer Res Jan. 1992;83(1):52–60.
Nyunoya et al., Virology Dec. 1988;167(2):538–44.
Qiu et al., Biotechnol Appl Biochem 1995; 21 (Pt 1):67–75.
Sekine et al., Gene May 30, 1988;65(2):187–93.
Tada et al., Virus Res Mar. 1988;9(4):357–67.
Sehgal, D.and Gopinathan, K.P., *Biotechniques*, vol. 25, No. 6, Dec. 1998, pp. 997–1006.
Xiao, Hua et al., *Proceedings of the National Academy of Sciences of the United States*, vol. 95, No. 5, Mar. 3 1998, pp. 2146–2151.

VP29+VP28  VP29+VP20 vBmfTIP30
U  CoT  P1  PC f-TIP30 →

1  2  3  4

His-TAT  -  4X  -  1X 2X 4X
f-TIP30  +  -  +  +  +  +
GST-CTD  -  +  +  +  +  +

← GST-CTD 1 2 3 4 5 6

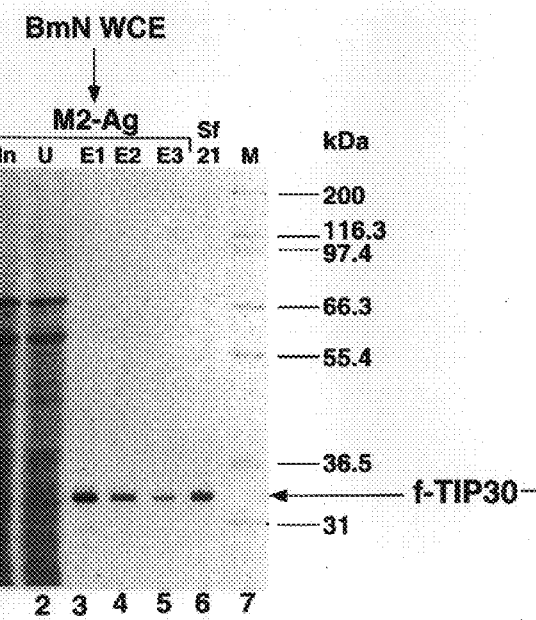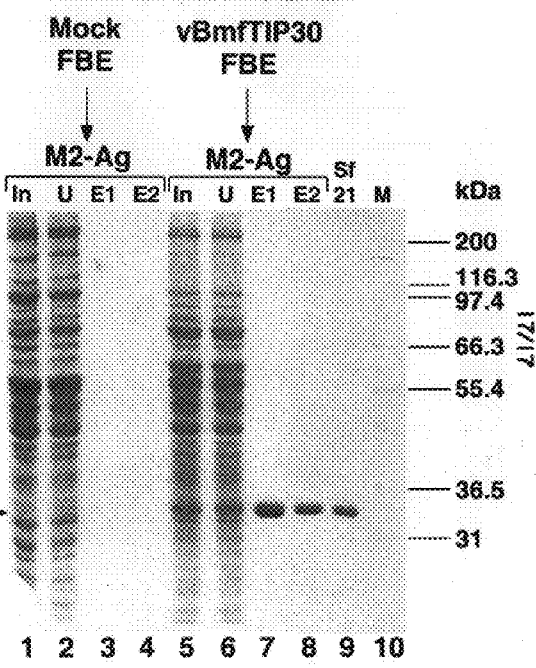

SYSTEM FOR RAPID GENERATION OF RECOMBINANT BACULOVIRUS-BASED EXPRESSION VECTORS FOR SILKWORM LARVAE

This patent application claims the priority of U.S. provisional patent application No. 60/159,707, filed on Oct. 15, 1999, which is incorporated herein by reference.

The present invention was supported, in part, by National Institutes of Health Grant Nos. CA 42567 and AI 37327. Accordingly, the U.S. Government has certain rights in this invention.

FIELD OF THE INVENTION

Recombinant expression systems for the production of proteins, and particularly a system for rapidly generating recombinant silkworm baculoviruses. Bombyx mori nuclear polyhedrosis virus (BmNPV) with an efficiency approaching 100% has been developed.

BACKGROUND OF THE INVENTION

Since the advent of recombinant DNA technology, there has been steady growth in the number of systems available for the regulated expression of cloned genes in prokaryotic and eukaryotic cells. One eukaryotic system that has gained particularly widespread use is the baculovirus expression vector system, or BEVS, developed by Smith, G. E., and Summers, M. D., U.S. Pat. No 4,745,051).

The baculovirus expression vector system (BEVS) has now emerged as the preferred system for production of recombinant eukaryotic proteins in insect cells. Two major reasons for its wide spread popularity have been the high yields of recombinant proteins in a biologically functional form and minimal biohazard potential. BEVS employs strong viral promoters (polyhedrin or p10) for foreign gene expression in insect cells or larvae infected with a recombinant baculovirus. There are two types of baculovirus-based expression systems: the popular *Autographa californica* nuclear polyhedrosis virus (AcNPV) that infects Sf9/Sf21 cells and *Trichoplusia ni* larvae, and the *Bombyx mori* nuclear polyhedrosis virus (BmNPV) that infects silkworm cells (BmN) and larvae (*Bombyx mori*). Baculoviruses only infect insects and are further restricted by species-specific barriers, i.e., AcNPV will not infect BmN cells or silkworm larvae and BmNPV will not infect Sf9 cells.

The Family Baculoviridae have large, circular, double-stranded DNA genomes (at least 90–230 kilobases (Francki, R. I. B., et al., eds., in Archives of Virology, (1991), Supp. 2, pages 117–123. There are two Subfamilies, Nudibaculovirinae, which do not form occlusion bodies, and the Eubaculovirinae, are characterized by their ability to form occlusion bodies in the nuclei of infected insect cells. The structural properties of the occlusion bodies are used to further classify the members of this Subfamily into two genera: the nuclear polyhedrosis viruses (NPVs) and the granulosis viruses (GVs).

In nature, baculovirus-infected cells produce extremely high quantities of two major very late gene products polyhedrin (polh) and p10; which comprise 40–50% of the total cellular protein by the end of the infection cycle. Very late in infection (both in insects and tissue culture) a large proportion of the cellular transcriptional activity is dedicated to the polh and p10 promoters, which makes them ideally suited for driving high level expression of foreign genes that replace these non-essential viral genes. Yields up to 100 mg target protein per $10^9$ cells or 50 silkworm larvae can be obtained. Viruses that lack the protective polyhedrin gene are innocuous in insects per Os (natural route of infection) but perfectly capable of establishing an infection when injected into the larvae manually. Hence, from an environmental, laboratory, manufacturing, and production point of view the silkworm larval system represents the safest system available to produce recombinant proteins and poses no threat to the sericulture industry.

The very late phase of baculovirus infection is distinct from the late phase of infection when budded viruses are formed. Consequently, expression of foreign proteins does not interfere with infectious virus production and virus replication. Target proteins can be directed to the appropriate subcellular location (including the cytoplasm, endoplasmic reticulum (ER), Golgi, plasma membrane, and nucleus) or secreted. Signal peptides of mammalian, plant, and yeast origin have been shown to direct proteins into the ER and to be properly cleaved in baculovirus-infected cells. Insect cells are capable of several post-translational modifications, which may be necessary to make some eukaryotic proteins functionally active. Myristoylation, phosphorylation, amidation, addition of fatty acids, sialylation, amino terminal and other eukaryotic protein modifications occur in baculovirus-infected cells. Glycosylation patterns are similar, but not identical, to those of mammalian cells. N-linked glycans (short or large mannose type) are added, as in mammals. Although, complex glycans are not formed, newer strains of engineered insect cells help overcome this deficiency. The silkworm larva-BmNPV based BEVS offers an additional advantage over Sf9-AcNPV based BEVS because of the possibility of expression in a variety of host cell types, thereby increasing the repertoire of post-translational modifications available for processing the recombinant proteins into their biologically functional form. Sf9 cells, being ovarian in origin, have a dedicated and limited capability of post-translational modifications in comparison to the silkworm larva.

The viral genome is very large (130 kb) and not amicable to direct manipulation, hence, the standard procedure for generating viral expression vectors has been to co-transfect insect cells with viral DNA and DNA of a transfer vector bearing the foreign gene under the control of the polhedrin promoter. Homologous recombination in vivo can replace a segment of the viral DNA by the modified sequence from the transfer vector, albeit at a very low frequency (0.1%–1%). Screening to identify a recombinant virus and separating it from parental virus can therefore involve considerable time and effort. Several modifications of this procedure that facilitate the identification of recombinant viruses by placing a reporter cassette adjacent to the gene to be expressed (Vialard et al., J. Virol. 1990; 64: 37–50; Vlak et al., Virol. 1990; 179: 312–320;Weyer et al., J. Gen. Virol. 1990; 71: 1525–1534 and Zuidema et al., J. Gen. Virol. 1990, 71: 2201–2209) or that increase the proportion of recombinant viruses (Kitts et al., Nucleic Acids Res. 1993; 18: 5667–5672; Peakman et al., Nucleic Acids Res. 1989; 13: 5403 and Kitts and Possee, Biotechniques 1993; 5:810–817) have been described. Recently, systems have also been developed for generating recombinant baculoviruses in yeast (Patel et al., Nucleic Acids Res. 1992; 20: 97–104.), *E. coli* (Luckow et al., J. Virol. 1993; 67: 4566–4579) or in vitro (Peakman et al., Nucleic Acids Res. 1992; 20: 495–500). A major bottleneck in the wide spread use of the BmNPV-based BEVS has been the tedious, time consuming plaque purification procedure required to isolate recombinant BmNPV expression vectors.

The major advantage of the BmNPV based expression system is that it can easily be expanded to an economical in vivo system using silkworm larvae. Because of its economic importance, the silkworm has been domesticated for thousand of years and techniques for mass rearing have been well-established. The silkworm larvae offers several additional advantages, e.g., it is easy to rear, it is easy to manipulate because of its large size, it has a relatively short life cycle (approximately 7 weeks), and its genetics and molecular biology have been well documented. The availability of artificial diets, availability of automated rearing equipment, and the fact that the larvae are non-allergenic to human handlers makes scale-up and mass production of recombinant proteins under sterile conditions very attractive in silkworm larvae. The silkworm BEVS has been applied for the production of useful biomolecules, such as pharmaceuticals, vaccines, enzymes, hormones, active viral insecticides, etc.

Foreign genes have been expressed using the AcNPV vector and their lepidopteran hosts, e.g., *Trichoplusia ni* and *Heliothis virescens*. These species, however, are significantly smaller than *B. mori*, and often cannibalistic, so that special rearing conditions are required. Hence, for high yields and cost effective production of recombinant proteins in larval hosts the BmNPV-*B. mori* expression system is the best option.

However, a major bottleneck in the BmNPV-based BEVS has been the tedious, time consuming plaque purification procedure required to isolate recombinant BmNPV expression vectors. Thus, there is a need in the art to overcome this obstacle and to provide an efficient system for rapidly generating recombinant BmNPV expression vectors.

The present invention addresses these and other needs in the art.

SUMMARY OF THE INVENTION

The invention provides an efficient and economical expression system for production of recombinant proteins in silkworm cells in tissue culture and in silkworm larvae. This system bypasses the bottleneck to expression in this otherwise attractive system, thus addressing a need in the art. In particular, the system of the invention ensures that recombinant vectors lack parental vector contaminants and include the gene of interest.

Thus, the invention provides a recombinant *Bombyx mori* nuclear polyhedrosis virus (BmNPV). This BmNPV has a genome comprising a restriction endonuclease site in a polyhedrin promoter region and a second restriction endonuclease site in an essential gene region located downstream of the polyhedrin promoter region, wherein the restriction endonuclease sites are not found outside of the segment of the genome delineated by the restriction endonuclease sites in the polyhedrin promoter region at the upstream end and the essential gene region in the down stream end, and wherein cutting of the genome by a restriction enzyme specific for the restriction site in the essential gene knocks out function of the essential gene. Preferably the restriction sites are the same. More preferably, the BmNPV contains an additional restriction site in the essential gene, such that treatment with the restriction endonuclease results in deletion of a majority of the C-terminus of the essential gene. In addition, the BmNPV contains a reporter gene, preferably luciferase reporter, under control of the polyhedrin promoter. This reporter gene can also contain the restriction site.

In addition, the invention provides a linear BmNPV created by restriction cutting of the BmNPV described above by the restriction endonuclease specific for the restriction sites in the polyhedrin promoter and the essential gene.

Thus, a linear BmNPV has one end comprising a cut restriction endonuclease site in a polyhedrin promoter region and a second end comprising a second cut in a restriction endonuclease site in an essential gene region.

A method for preparing a recombinant *Bombyx mori* nuclear polyhedrosis virus (BmNPV) as described above is also provided. The method comprises introducing a restriction site into the polyhedrin promoter; introducing a restriction site into the essential gene; and selecting recombinant BmNPV that contain both restriction sites.

To reconstitute an effective expression system, the linear BmNPV is co-transfected with a transfer vector that rescues the virus by providing the essential gene. Thus, the invention provides a transfer vector comprising a region of an BmNPV genome containing or upstream of a polyhedrin promoter, a cassette insertion site operably associated with the polyhedrin promoter or another promoter effective in silkworm cells, and a region of a BmNPV genome containing an essential gene, wherein the essential gene is located downstream of the polyhedrin promoter in a wildtype BmNPV genome and is oriented in the transfer vector the same way relative to the polyhedrin promoter as it is in wildtype BmNPV, and wherein the two regions are of sufficient size to permit homologous recombination with a BmNPV vector.

*Bombyx mori* (silkworm) cell transfected with the BmNPV, and preferably co-transfected with the BmNPV and the transfer vector in which a gene of interest is inserted into the cassette insertion site is also provided. The *B. mori* cell can be a BmN cell in tissue culture or it can be in a silkworm larva.

The co-transfected silkworm cells permit expression of the protein encoded by the gene of interest. Thus, in another embodiment the invention provides a method for producing a protein encoded by a gene of interest, which method comprises isolating the protein expressed by the BmN cell cultured under conditions that permit expression of the protein encoded by the gene of interest, or expressed by a silkworm larva infected with a recombinant BmNPV and reared under conditions that permit expression of the protein encoded by the gene of interest. In one embodiment the protein is isolated from fat body extracts. In another embodiment, the expressed protein includes a secretory signal and is isolated from interstitial fluid. In still another embodiment, the expressed protein is an HIV TAT interacting protein (f-TIP30).

These and other aspects of the invention are more fully developed in the accompanying Drawings, Detailed Description, and Examples.

BRIEF DESCRIPTION OF THE DRAWINGS

FIG. 10. SDS-PAGE analysis of affinity-purification and quantitation of recombinant f-TIP30 from BmN cells and *B. mori* larvae fat bodies. A) Aliquots of the input (In), unbound (U), eluates 1,2 and 3 (E1,E2,E3) and recombinant f-TIP30 purified from Sf21 cells infected with vAcf-TIP30 (Sf21) were analyzed. B) f-TIP30 was also purified from *B. mori* larvae fat bodies extract (FBE). Mock infected FBE served as control for the purification procedure. The input, unbound and eluate lanes were as marked in (A) above.

DETAILED DESCRIPTION OF THE INVENTION

The recombinant *B. mori* nuclear polyhedrosis virus (BmNPV) system of the invention, termed "Bombyx Easy", provides a positive selection for recombinant BmNPV vectors. As noted above, this system bypasses the bottleneck to expression in this otherwise attractive system, thus addressing a need in the art. In particular, the system of the invention ensures that recombinant vectors lack parental vector contaminants and include the gene of interest.

In a specific embodiment, the Bombyx Easy BEVS was used to generate vBmf-TIP30 a recombinant baculovirus expression vector for expressing FLAG epitope-tagged TIP30 (an HIV TAT interacting protein isolated from HeLa cells) (Xiao, et al., Proc. Natl. Acad. Sci. USA 1998; 95: 13519–13524) in BmN cells and silkworm larvae. We describe the construction of vBmf-TIP30 from Bsu36I digested-vBmBEIII DNA with 100% efficiency and have confirmed its purity by PCR. f-TIP30 was purified from BmN cells and silkworm larvae fat body extracts in a single step by affinity (M2-Agarose) chromatography. Authenticity of the recombinant f-TIP30 was confirmed by western blot using a f-TIP30 specific antibody. Functional activity of recombinant f-TIP30 was confirmed by in vitro kinase assays (Xiao et al., EMBO 2000; 19: 956–963). The most striking feature of the BmNPV BEVS was the high level of expression (approaching 1 mg/larva) and the high yields of purified protein (at least 3 mg from 50 larvae). The advent of Bombyx Easy system coupled with the high yields from silkworm larvae should make it an attractive alternative to the expensive cell culture based AcNPV BEVS. The Bombyx Easy system is the first and only available system for rapidly generating recombinant BmNPV-based expression vectors.

Figure 1:
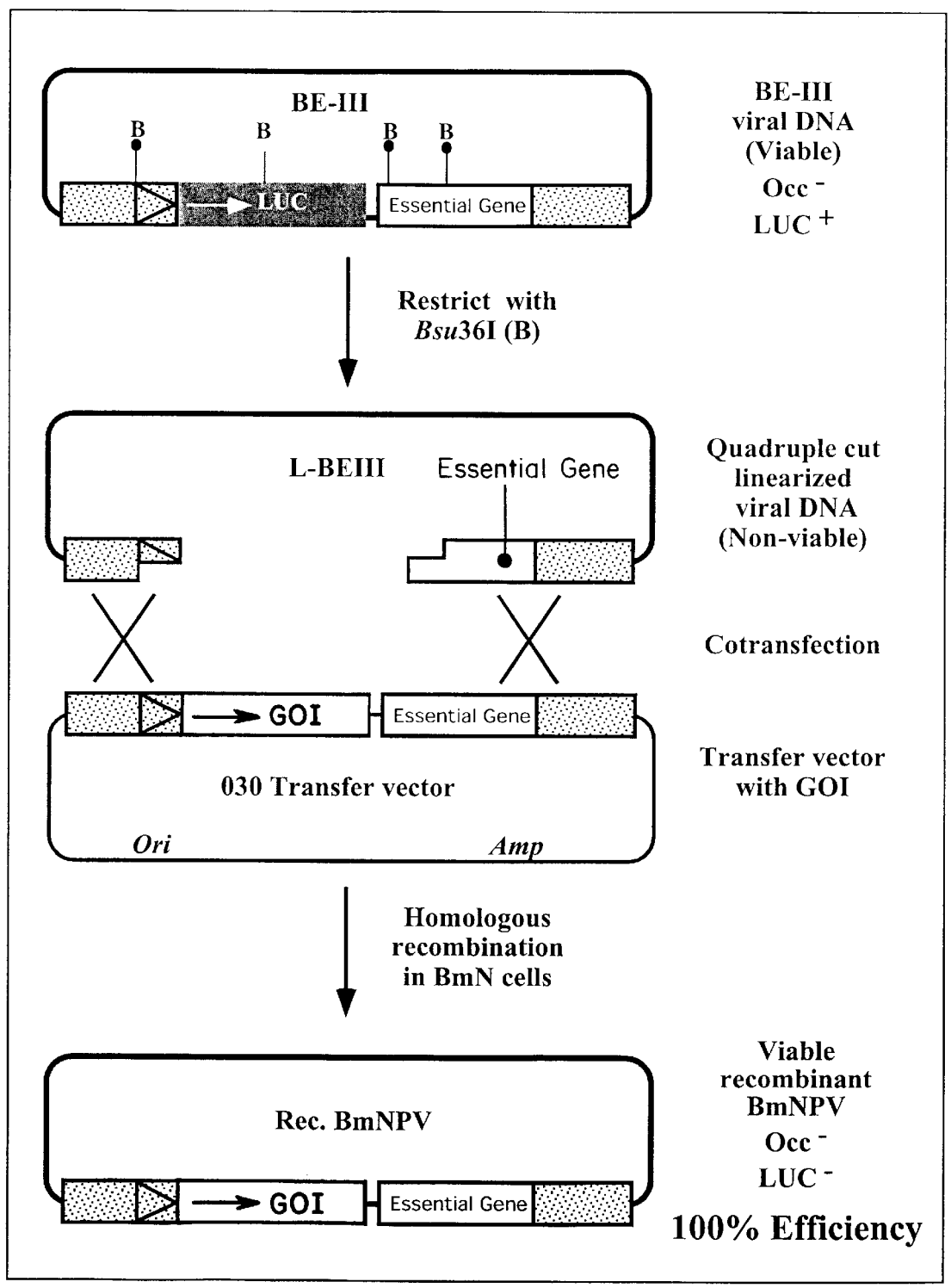
FIG. 1. Schematic figure showing positive selection strategy, which forms the basis of the Bombyx Easy (BEIII) system. L-BEIII indicates linearized BEIII (after treatment with Bsu36I). "B" indicates a Bsu36I restriction site in the construct. Mottled bars depict homolgous sequences. The ">" arrow indicates the polyhedrin promoter. "LUC" refers to luciferase. "GOI" stands for "gene of interest."

FIG. 1 shows a specific embodiment for the invention. This invention is based, in part on construction of a system that depends on rescuing an essential gene (such as, ORF 1629) present downstream to the polyhedrin expression locus. A BmNPV derivative, BEIII-Luc, was constructed in which three Bsu36I restriction sites were introduced within the polyhedrin flanking sequences (one in the promoter and two within ORF 1629), and a fourth Bsu36I site was included within the luciferase gene. Site directed mutagenesis was carried out silently, without disturbing the amino acid sequences. Hence, the parental viruses are viable but restriction of the circular viral genome with Bsu36I restriction endonuclease linearizes it with 100% efficiency, deleting an essential part of the viral genome and rendering the viruses non-viable. Transfer vectors for introduction of a gene interest (GOI) carry a copy of this deleted region downstream from the site into which foreign genes are inserted for expression. Recombination between the transfer vector and linearized viral DNA restores the integrity of the essential gene. All the viable viruses are recombinant viruses containing the foreign gene at the expression locus. Therefore, recombinant viruses have a selective advantage over non-recombinant linearized viral DNA. Since such a high proportion of the viruses obtained by co-transfecting transfer vector DNA and linearized BEIII-Luc viral DNA express the foreign gene, the tedious plaque purification normally used to select recombinant baculoviruses can be circumvented. The absence of luciferase activity in cells infected with the recombinant virus helps confirm the purity of recombinant virus stocks. The Bombyx Easy system greatly reduces the time required to isolate recombinant BmNPV expression vectors.

As shown in the Examples, infra, we have expressed and purified FLAG epitope-tagged HIV TAT interacting protein of 30 kDa (f-TIP30) from *B. mori* (BmN) cells in culture and silkworm larvae. Authenticity of the pure recombinant protein was confirmed by Western blots, and its biological activity was confirmed by in vitro kinase assays. In a single step, at least 3 mg of recombinant f-TIP30 could be purified from fat body extracts of 50 silkworm larvae infected with recombinant BmNPV. Such high yields of recombinant proteins made economically in silkworm larvae, coupled with the high efficiency of rapidly generating recombinant baculoviruses employing the Bombyx Easy system, should now make the BmNPV-silkworm larvae based expression system an attractive alternative to the conventional AcNPV-Sf9 cells based baculovirus expression system.

The present invention provides significant differences and advantages in comparison to linearized AcNPV DNA. For economic, high level expression of recombinant proteins in silkworm larvae an essential prerequisite is to generate recombinant BmNPV-based expression vectors. Since there is a species-specific barrier that prevents AcNPV from establishing a viable infection in silkworm cell lines or larvae, it is obligatory to develop an efficient system for producing recombinant BmNPV. The Bombyx Easy incorporates advantages include:

1. The Bombyx Easy system is the first and only available system for rapidly generating recombinant BmNPV-based expression vectors.

2. In a specific, preferred embodiment, the vBmBEIII genomic DNA harbors four restriction sites (e.g., Bsu36I) compared to the three sites present in the AcNPV system. The additional site in vBmBEIII was inserted deeper into the C-terminal end of the essential gene ORF1629, such that a much larger deletion of the C-terminal end of ORF1629 could be achieved and thus ensure that the linearized parental viral DNA is nonviable.

3. Having a fourth site improves the probability and efficiency of Bsu36I restriction digestion, which helps eliminate any background contamination from uncut viral DNA. This zero background from 100% linearized vBmBEIII DNA provides a major advantage in using the Bombyx Easy system, as it eliminates the need for plaque purification of recombinant viruses and increases throughput.

4. In a preferred embodiment, vBmBEIII employs luciferase as the reporter gene instead of the conventional β-Gal gene used in the AcNPV based system. The more sensitive luciferase assay not only helps in the purification of vBmBEIII but also gives the Bombyx Easy system the advantage of easily detecting any parental virus contamination in recombinant virus stocks due to incomplete parental DNA Bsu36I digestion.

As used herein, a "*Bombyx mori* polyhedrosis virus genome" is a circular DNA that contains the genomic sequence of *B. mori* nuclear polyhedrosis virus (BmNPV). A "wildtype" genome is an BmNPV genome found in nature, i.e., in viral isolates from infected silkworms (or other permissive hosts).

A BmNPV is "recombinant" when it has been manipulated or engineered to contain restriction endonuclease sites in the polyhedrin promoter region and an essential gene region located downstream of the polyhedrin promoter. The term "downstream" with respect to the essential gene refers to its orientation relative to the operational direction of the polyhedrin promoter. However, as shown in FIG. 4, the essential gene is oriented in the opposite direction relative to the polyhedrin promter.

The term "region " is used to refer to a part of the genome containing a sequence of interest, such as the polyhedrin promoter, the essential gene or part of the essential gene, etc. The use of the term region reflects that certain modifications to create the recombinant BmNPV can be made in any location, provided that the desired effect of cutting (deletion of enough of the essential gene to render it non-functional, for example) will occur. However, it is preferable to engineer restriction sites that do not affect the encoded amino acid sequence, i.e., create silent site directed mutations in the target region of the BmNPV genome. In this embodiment, as a practical matter, the actual location of the modification in any particular region will depend on where the modification can be made "silently."

An "essential gene" is a gene necessary for BmNPV function, i.e., replication. Deletion of an essential gene "knocks out function" when the deletion results in expression of such a small part of the gene that the protein is unable to perform the same functions as the wildtype gene, even at a reduced or partial level, or that the remaining part of the gene is not translated, or if translated, it is not transcribed. In a preferred aspect of the present invention, a majority of the C-terminus, and about 30% of the ORF 1629 gene, is deleted after cutting by the restriction enzyme whose site was incorporated in the essential gene.

Cutting with the restriction enzyme yields a "linear BmNPV." This linear BmNPV will have ends corresponding to the restriction site; such ends may have overhanging sequences. The key to creation of a linear BmNPV for practice of the invention is the lack of the restriction sites in the BmNPV backbone outside of the region between the polyhedrin promoter and the essential gene, i.e., downstream of the polyhedrin promoter region and upstream of the essential gene region, oriented relative to the promoter.

Effective expression of a protein encoded by a gene of interest by the BmNPV vector depends on recombination of the linear BmNPV genome with a transfer vector. The transfer vector carries the gene of interest (which is inserted in a cassette insertion site) operably associated with a promoter that permits expression in a silkworm cell infected with BmNPV, e.g., the polyhedrin promoter. The gene of interest is downstream of a recombination site that will homologously recombine with the linear BmNPV in the polyhedrin promoter region. The gene of interest is upstream of a recombination site that will homologously recombine with the linear BmNPV in the essential gene region. Generally, for homologous recombination, the DNA will be at least about 1 kilobase (kb) in length and preferably 3–4 kb in length, thereby providing sufficient complementary sequence for recombination. The key to the success of this transfer vector is that it contains a functional essential gene downstream of the gene of interest. Thus, recombination of the transfer vector with the linear BmNPV will yield a functional BmNPV vector by rescue of the linear BmNPV genome by the essential gene. Parental BmNPV will not function, thus plaque purification is unnecessary. Improperly recombined vectors will be non-functional. They will also express a reporter gene, in the case of a preferred embodiment where the recombinant BmNPV contains a reporter gene.

A "gene of interest" is any gene encoding a desired protein. Examples of desired proteins are set forth below. In a specific embodiment, the gene of interest encodes an HIV TAT interacting protein (f-TIP30). A "reporter gene" is a gene that permits ready detection of its expression. It can be a positive selection gene, i.e., that provides protection from an antibiotic, but preferably is a gene that produces a signal. In a preferred embodiment, the reporter gene is luciferase. Other possible reporter genes include, but are by no means limited to, chloramphenicol transferase (CAT), β-galactosidase (β-gal), green fluorescent protein, alkaline phosphatase, and other genes that can be detected, e.g., immunologically (by antibody assay).

The term "infectious" refers to the ability of a virus to replicate in a cell and produce viral particles. In one embodiment, plaque formation of cells in cell cultures evidence that a viral construct is infectious. Plaque formation is also termed "cytopathic effect" or "cell lysis". The analogous effect in vivo is development of either an acute or chronic viral infection, which may include either overt pathology or merely replication and propagation of the virus in an infected animal. In another embodiment, detection of expressed proteins form the chimeric viral genome indicates that the viral construct is infectious.

The term "permissive" refers to a cell which permits the replication of a particular virus.

The term "non-permissive" refers to a cell that does not permit replication of a particular virus.

As used herein, the term "isolated" means that the referenced material is removed from the environment in which it is normally found. Thus, an isolated biological material can be free of cellular components, i.e., components of the cells in which the material is found or produced in nature. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. As used herein, a membrane protein expressed in a heterologous host cell (i.e., a host cell genetically engineered to express the membrane protein), such as a LDLR, is regarded as "isolated." An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, particularly in biology, the term "about" can mean within an order of magnitude of a given value, and preferably within one-half an order of magnitude of the value.

The following abbreviations are used throughout this application:

BmNPV—*Bombyx mori* nuclear polyhedrosis virus
AcNPV—*Autographa californica* nuclear polyhedrosis virus
bp—base pairs
BEVS—baculovirus expression vector system
ECV—extracellular virus
GV—granulosis virus
kDa—kilodaltons
NPV—nuclear polyhedrosis virus
occ⁻—occlusion negative virus(es)
occ⁺—occlusion positive virus(es)
OV—occluded virus
PCR—polymerase chain reaction
pfu—plaque forming unit
p.i.—post-infection
PIB—polyhedrin inclusion body (also known as occlusion body)
5' UTR: The mRNA or gene sequence corresponding to the region extending from the start site of gene transcription to the last base or base pair that precedes the initiation codon for protein synthesis.
3' UTR: The mRNA or gene sequence corresponding to the region extending from the first base or basepair after the termination codon for protein synthesis to the last gene-encoded base at the 3' terminus of the mRNA.
(+)strand: Refers to the DNA strand of a gene and its flanking sequences which has the same sense as the RNA that is derived from that gene.
(−)strand: Refers to the DNA strand of a gene and its flanking sequences that is complementary to the (+)strand.

Molecular Biology

In accordance with the present invention there may be employed conventional molecular biology, microbiology, and recombinant DNA techniques within the skill of the art for the production of recombinant proteins. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis

[M. J. Gait ed. (1984)]; Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; A Practical Guide To Molecular Cloning [B. Perbal (1984)]; Current Protocols in Molecular Biology, John Wiley & Sons, Inc. [F. M. Ausubel et al (eds.) (1994)].

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. In discussing the structure of particular nucleic acid molecules, sequences or regions may be described herein according to the normal convention of giving only the sequence in the 5' to 3' direction. A "recombinant DNA molecule" is a DNA molecule that has undergone a molecular biological manipulation.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene is heterologous to the vector DNA in which it is inserted for cloning or expression, and it is heterologous to a host cell containing such a vector, in which it is expressed, e.g., insect cells.

The term "host cell" means any cell of any organism that is capable of infection by or propagation of a virus construct of the invention. Generally, host cell herein means a silkworm host cell.

The term "gene" means a DNA sequence that codes for or corresponds to a particular sequence of amino acids which comprise all or part of one or more proteins or enzymes. A gene can also include non-coding sequences, such as introns, 5'-UTR and 3'-UTR. It may, but for purposes of the present invention, need not include non-transcribed sequences upstream and downstream of the transcribed region.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Examples of promoters which can be used in the practice of this invention are baculovirus late or very late promoter. In general, the early genes include those that (a) have been identified empirically as being expressed during the early phase (i.e., before DNA synthesis) of the replication cycle of an insect virus, such as a AcMNPV replication cycle or (b) are predicted to be expressed early in the insect virus life cycle (e.g. AcMNPV life cycle) based on the presence of enhancer-like elements, conserved cap sequences and/or TATA box sequences in the first 160 bp upstream of the ATG start codon of the gene, or (c) are homologs of AcMNPV early genes in other nuclear polyhedrosis viruses. A listing of the genes meeting these criteria in AcMNPV has been presented by Ayres et al. ("The complete DNA sequence of *Autographa californica* nuclear polyhderosis virus," Virology A94, 202:586–605), which is incorporated herein by reference.

A coding sequence is "under the control" or "operatively associated with" of transcriptional and translational control sequences in a cell when RNA polymerase transcribes the coding sequence into mRNA, which is then trans-RNA spliced (if it contains introns) and translated into the protein encoded by the coding sequence.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a mRNA or a protein. The expression product itself, e.g. the resulting protein, may also be said to be "expressed" by the cell.

The term "expression system" means a host cell and compatible vector under suitable conditions, e.g. for the expression of a protein coded for by foreign DNA carried by the vector and introduced to the host cell. As used herein, an expression system comprises a recombinant BmNPV generated by recombination of the linearized recombinant BmNPV and the transfer vector in a permissive insect cell, e.g., a silkworm cell.

"Sequence-conservative variants" of a polynucleotide sequence are those in which a change of one or more nucleotides in a given codon position results in no alteration in the amino acid encoded at that position. Sequence conservative variants encoding any of the proteins described herein may be useful in various expression systems, e.g., to incorporate preferred codons in the coding sequence so as to increase expression efficiency, or to incorporate a restriction site to facilitate manipulation of the coding sequence without altering the amino acid sequence.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). A "function-conservative variant" also includes a truncated or form of the protein that performs its function.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides The term "transfection" means the introduction of a foreign nucleic acid into a cell. The introduced gene or sequence may also be called a "cloned" or "foreign" gene or sequence, may include regulatory or control sequences, such as start, stop, promoter, signal, secretion, or other sequences used by a cell's genetic machinery. A host cell that receives and expresses introduced DNA or RNA has been "transformed" and is a "transformant".

Genes of Interest

The Bombyx mori baculovirus expression vector systems can be used successfully to express genes of interest isolated from a wide range of prokaryotic and eukaryotic organisms and viruses. Some representative examples include the expression of a number of human genes including growth hormone (hGH); macrophage colony-stimulating factor (hM-CSF); beta-interferon (HuIFN-beta); human alpha-interferon in Bombyx mori larvae and CD4 (T cell surface protein T4) replaced by the signal DNA sequence from the insect signal peptides coding for the cuticle gene or adipokinetic hormone (Kadono-Okuda et al., Biochem Biophys Res Commun 1995; 213(2):389–96; Qiu et al., Biotechnol Appl Biochem 1995; 21 (Pt 1):67–75; Deng et al., Chin J Biotechnol 1995;11(2):109–17; Maeda et al., Nature 1985; 315(6020):592–4; and U.S. Pat. Nos 5,278,050; 5,155,037 and 5,023,328). The silkworm larvae has also been used for the high-level expression and secretion of biologically active mouse interleukin-3 (Miyajima et al., Gene 1987;58(2–3): 273–81) and recombinant ookinete surface antigens of Plasmodium berghei (Matsuoka et al., Vaccine February 1996; 14(2): 120–6). A recombinant, full length keratinocyte growth factor (KGF) has been expressed in insect cell hosts including Bombyx mori. (U.S. Pat. Nos 5,863,767; 5,843, 883 and 5,773,586). A prokaryotic prolylendopeptidase from Flavobacterium has been expressed in insect cells using Bombyx mori nuclear polyhedrosis virus (BmNPV) (U.S. Pat. No 5,521,081).

Components from viruses have been expressed in the Bombyx mori baculovirus expression vector system. These include the fusion glycoprotein (F) from Newcastle disease virus (NDV) strain D26 (Mori et al., Avian Dis October–December 1994; 38(4):772–7); the kinase-active v-erbB gene, an oncogene of the avian erythroblastosis virus encoding a protein that is a truncated version of the epidermal growth factor receptor (Morishita et al., Jpn J Cancer Res January 1992; 83(1):52–60); hepatitis B and C virus antigens (Higashihashi et al., J. Virol. Methods November-December 1991; 35(2): 159–67 and U.S. Pat. Nos 5,734,019 and 5,714,314); characterization of v-sis protein (Morishita et al., J Biochem (Tokyo) January 1991; 109(1):36–44); recombinant proteins from human T-cell leukemia virus type I (HTLV-I) (Nyunoya et al., AIDS Res Hum Retroviruses November 1990; 6(11):1311–21 and Nyunoya et al., Virology December 1988; 167(2):538–44); and human papillomavirus type 6b E2 gene product with DNA-binding activity in insect (Bombyx mori) cells (Sekine et al., Gene May 30, 1988; 65(2):187–93 and Tada et al., Virus Res March 1988; 9(4):357–67). Finally, a recombinant expression Baculovirus vector capable of expression in a Bombyx mori host cells with improved insecticidal activity (U.S. Pat. No 5,674, 485).

In most cases, the proteins are biologically active and undergo appropriate post-translational modification, including proteolytic processing, glycosylation, phosphorylation, myristylation and palmitylation. Hence, this system has proven to be a highly valued tool for both fundamental molecular research and for the production of proteins for commercial purposes.

EXAMPLES

The invention will be better understood by reference to the following Examples, which are illustrative of the invention and are not intended to limit it in any way.

EXAMPLE 1

Generation of Recombinant BmNPV-based Expression Vectors

The Example demonstrates the rapid generation of Recombinant BmNPV Baculovirus based expression vectors for the high level expression of recombinant proteins in silkworm larvae and cells.

Materials and Methods

Viruses and cells. BmNPV (BGL) (Palhan, et al., Current Science 1996; 70: 147–153 and Palhan, Ph.D. thesis, 1995) and its derivatives vBmBEIII were propagated in BmN cells (Maeda, 1988, p. 167–181. In J. Mitsuhashi (Ed.), Invertebrate Cell System Applications—Vol. I. CRC Press, Boca Raton) at 28° C. using TC-100 medium (Life Technologies) supplemented with 10% fetal calf serum. Standard procedures for growing BmNPV derivatives, plaque assays for the determination of viral titer and analyzing infected cell DNA were followed. (Maeda, 1988, supra, Palhan et al., 1995, supra and Choudary et al., 1995, p. 243–264. In Richardson C. D. (Ed.) Methods in Molecular Biology, Vol 39: Baculovirus Expression Protocols, Humana Press, Totowa, N.J.).

Rearing silkworms. *Bombyx mori* eggs were purchased from Insect Lore (CA) and reared on mulberry leaves for the first three instars (the stage between molts) and then they were subsequently reared on an artificial diet (Choudary et al., 1995, supra). Larvae were injected with 10 µl of virus suspension ($10^5$ pfu) as described earlier (Palhan et al., 1995, supra and Choudary et al., 1995, supra). Five days post infection, the larvae were dissected and the fat bodies were isolated and sonicated on ice in five volumes of BC500 buffer [20 mM Tris-HCl (pH 7.9),20% glycerol, 500 mM KCl, 0.2 mM EDTA, 1 mM DTT] with 0.2% NP-40 using a Branson sonifier (50% cycle, micro tip, 4 times, 1 min each with a gap of 1 min). The sonicate was then clarified by centrifugation (14,000 rpm, 10 min at 4° C.) and the supernatant (fat bodies extract, FBE) was used for recombinant protein purification.

Restriction digests of viral DNA. Viral DNA was extracted from budded virus, purified by banding on cesium chloride gradients and dialyzed against TE (10 mM Tris-HCl, pH 8.0, 1 mM EDTA) (King and Possee, 1992. The Baculovirus Expression System: A Laboratory Guide. Chapman & Hall, New York.). vBmBEIII DNA (1 mg) was digested overnight with 10 units of Bsu36I (NEB) in 50 µl (1×NEB Buffer3 with BSA per the manufacturers recommendations) at 37° C. The enzyme was inactivated at 70° C. for 15 min and the digest was stored at 4° C. The aliquots of the digested and undigested viral DNAs were analyzed on a 0.5% agarose gel to check that the digest was complete (Kitts et al., Nucleic Acids Res. 1990; 18: 5667–5672.).

Co-Transfection of linearized viral and transfer vector DNAs. BmN cells ($10^6$) were seeded in a 35 mm dish and allowed to attach for 2 h. Bsu36I-digested vBmBEIII viral DNA (100 ng) and transfer vector DNA (500 ng) were mixed in a sterile polystyrene tube and lipofected using DOTAP, a liposomal transfection reagent (Roche Molecular Biochemicals) as described earlier (Palhan et al., Biotechniques 1995; 19: 97–104).

96-well LUC assay. BmN cells ($2 \times 10^4$ cells/well) were seeded in a 96-well plate and allowed to attach for 2 h. Virus suspension (10 µl) from either first round plaque assay selection or co-transfection supernatant serial dilutions ($10^{-5}$ to $10^{-7}$) were added to each well. Five days post infection, LUC assay buffer (Promega) was added to each well and the luminescence emitted was recorded by a live CCD camera in a dark room.

PCR analysis. Viral DNA was isolated from 0.75 µl of the infected cell supernatant and PCR analysis was setup as described earlier (Day et al., 1995, p. 143–159. In Richardson C. D. (Ed.) Methods in Molecular Biology, Vol 39: Baculovirus Expression Protocols, Humana Press, Totowa, N.J.). The oligonucleotides used for PCR analysis were as follows: Forward primers—VP 12, 5' ATAAC CATCT CGCAA ATAAA TAAG 3' (SEQ ID NO:1) and VP 29, 5' GTTTT TTATT AACCT CAGGA TATCA AATGG AAATA ATAACC 3' (SEQ ID NO:2); Reverse primers—VP13, 5' AATTG TCTGT AAATC AACAA CGC 3 (SEQ ID NO:3)'; VP 20, 5' GCCGA CGACT GTGTT GCCTA AG 3' and VP28 (SEQ ID NO:4), 5' CATTA AATTT GTAAT CCTTA GGGTG GTATG 3' (SEQ ID NO:5).

Figure 2A:
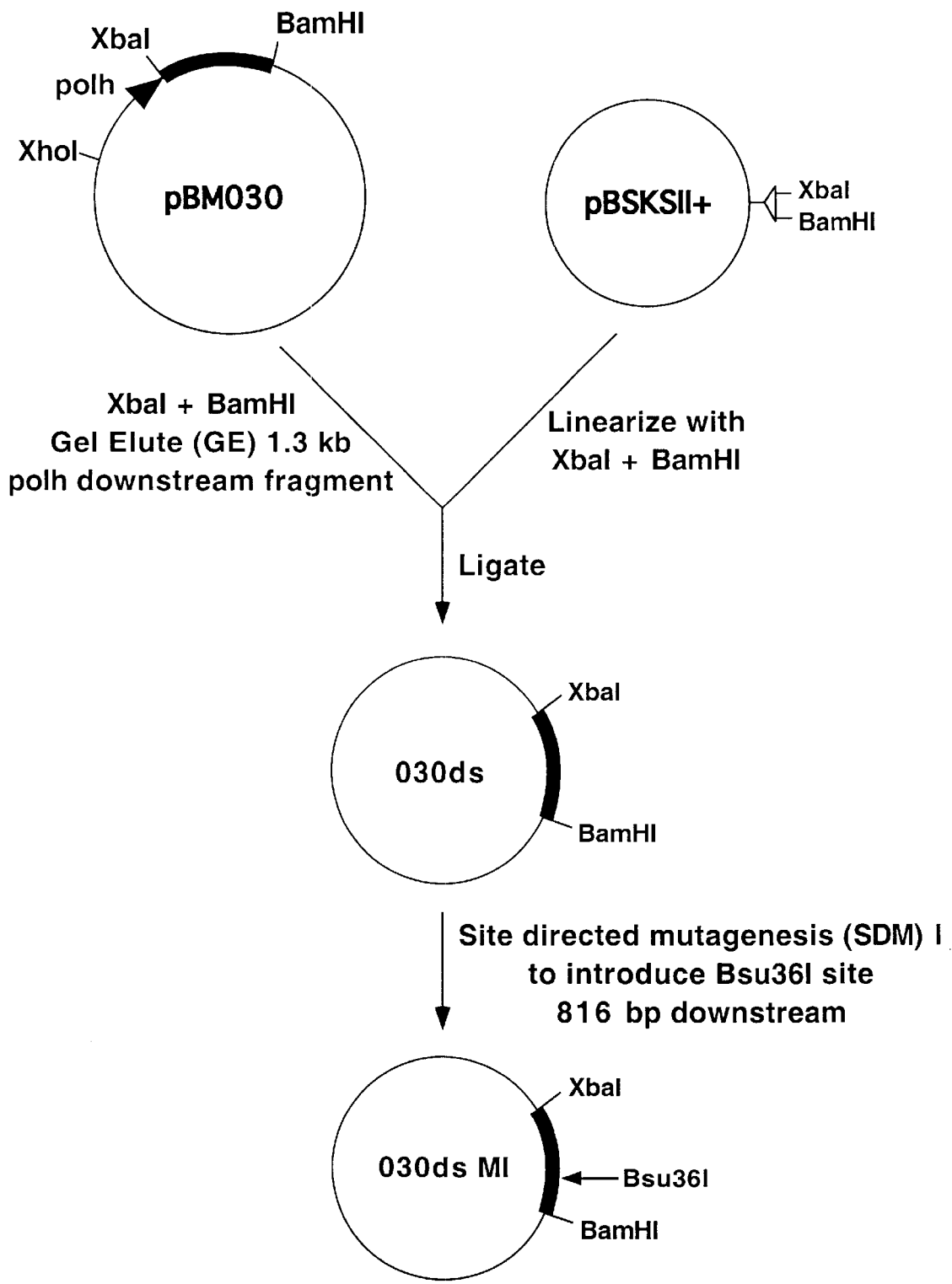
FIGS. 2A–H. Schematic figure showing the cloning strategy for engineering pBEIII.

Cloning strategy for engineering pBEIII. In order to introduce Bsu36I restriction sites within the essential gene ORF1629, present downstream to the polyhedrin gene, a 1.3 kb XbaI to BamHI fragment from the BmNPV transfer vector-pBm030 was subcloned into the pBluescriptII vector (Stratagene) linearized with the same enzymes. The resultant construct was called 030ds (FIG. 2A).

Using site directed mutagenesis (SDM) following the Quickchange protocol as per the manufacturer's (Stratagene) instructions, a Bsu36I restriction site was introduced into the ORF1629 by changing an "A" to "G" at nucleotide position 816 with respect to ATG of ORF1629 being +1 (or nt 1581 T to C wrt T3 genomic sequence). The sequence of the oligonucleotide used for mutagenesis was 5' GTG TTG <u>CCT AAG G</u>AG CCC AAA CG 3' (SEQ ID NO:6), the gaps represent the codons and the mutated base is shown in bold, the Bsu36I site is underlined. Incorporation of the Bsu36I restriction site was confirmed by restriction digestion and sequencing. This construct was called 030dsMI (FIG. 2A).

Figure 2B:
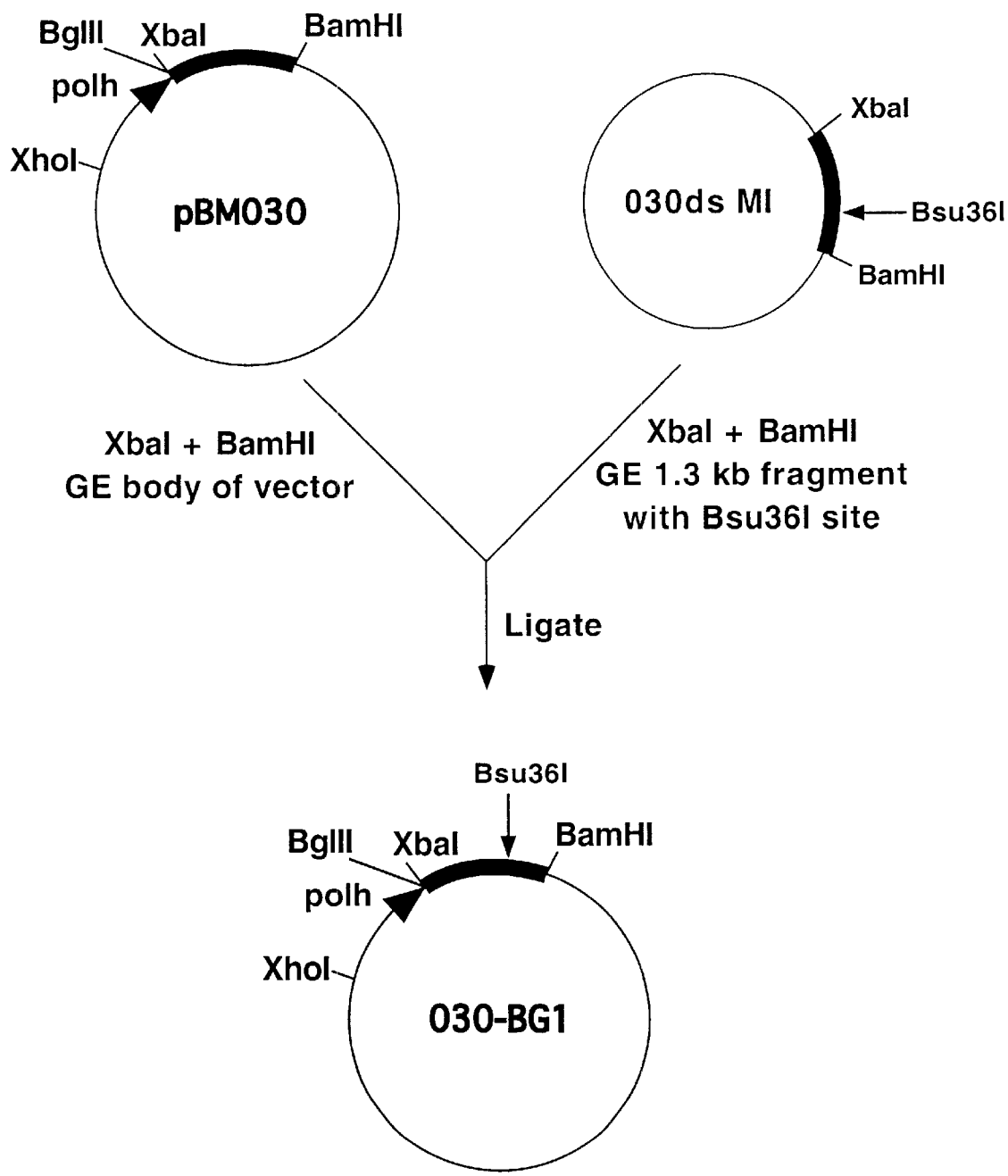

The Bsu36I site was mobilized back into pBM030 by replacing the XbaI-BamHI (1.3 kb) fragment from 030dsMI into pBM030. The resulting construct was called 030-BGI (FIG. 2B).

Figure 2C:
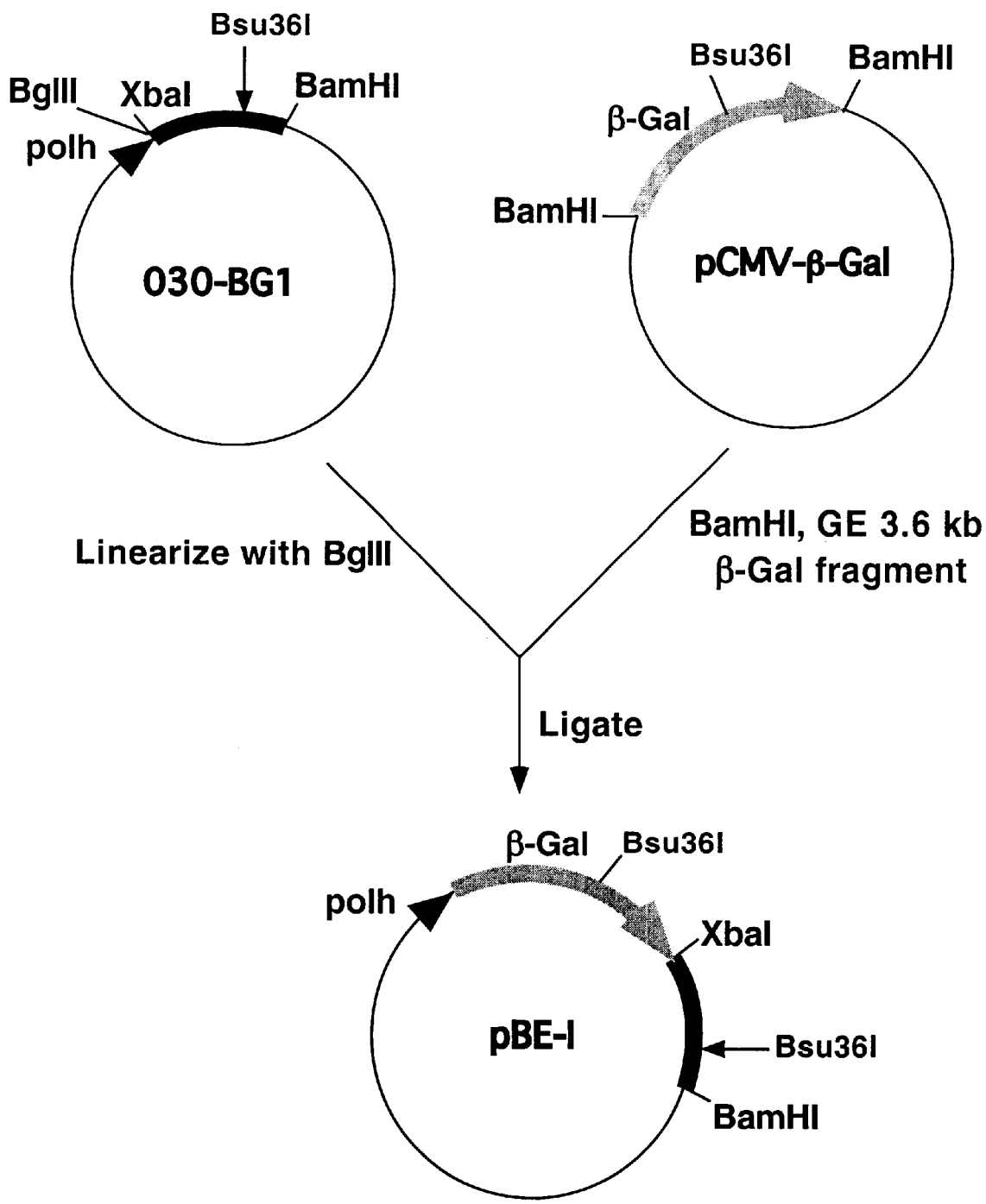

To allow plaques of the new virus to be recognized by a simple visual screen, the *E. coli* β-Galactosidase (β-Gal) gene, isolated as a 3.6 kb BamHI fragment from pCMVβ-Gal, was subcloned into the BglII site of 030-BGI. Correct orientation of the β-Gal gene with respect to the polyhedrin promoter was confirmed by restriction digestion. The resulting construct was called pBEI (FIG. 2C).

Figure 2D:
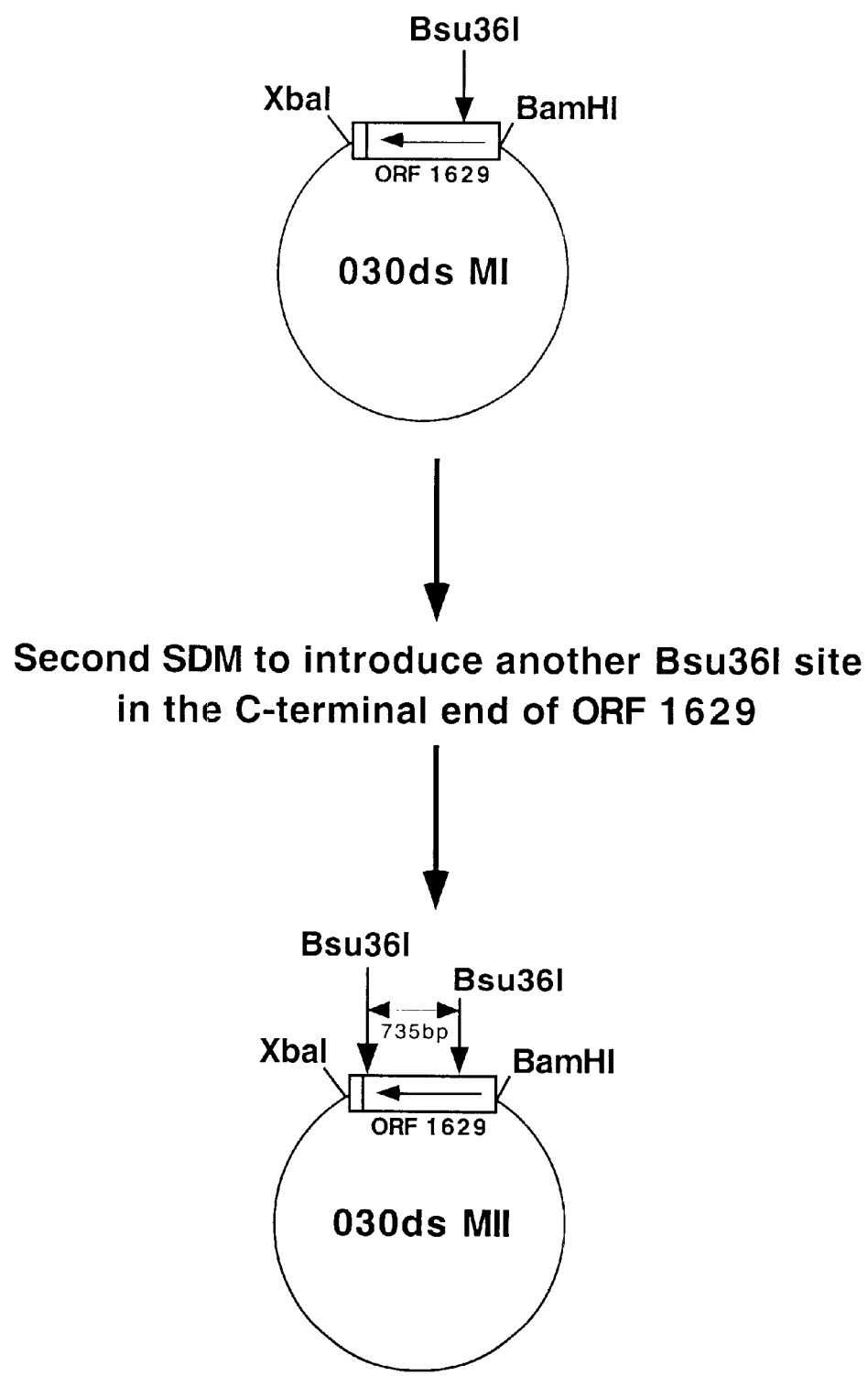

A second round of SDM was carried out on 030dsMI plasmid to introduce another Bsu36I site in the C-terminal end of ORF1629, thereby generating construct 030dsMII (FIG. 2D). This mutation changed an "A" to "G" at nucleotide position 1551 with respect to ATG of ORF1629 being +1 (or nt 845 T to C wrt T3 genomic sequence). The sequence of the oligonucleotide used for mutagenesis was 5' CA TAC CAC <u>CCT AAG G</u>AT TAC AAA TTT AAT G 3' (SEQ ID NO:7). The gaps represent the codons and the mutated base is shown in bold, the Bsu36I site is underlined. Restriction digestion of 030dsMII with Bsu36I released a 800 bp fragment thereby confirming the mutagenesis. This digestion would delete a major portion of the C-terminus of ORF1629.

Figure 2E:
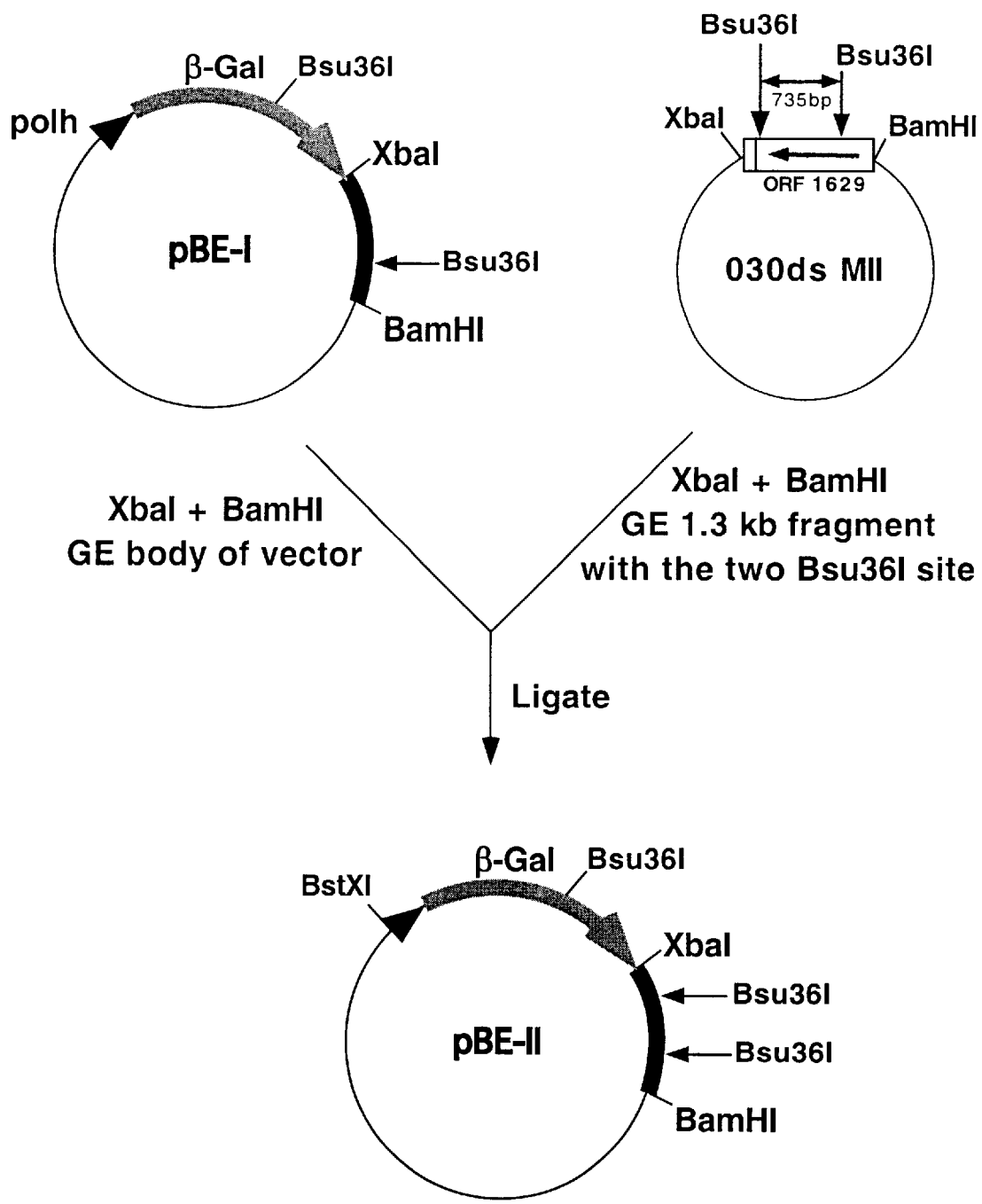

The two Bsu36I restriction sites were mobilized into pBEI by replacing the XbaI-BamHI (1.3 kb) fragment from 030dsMII into pBEI, the resulting construct was called pBEII (FIG. 2E).

Figure 2F:
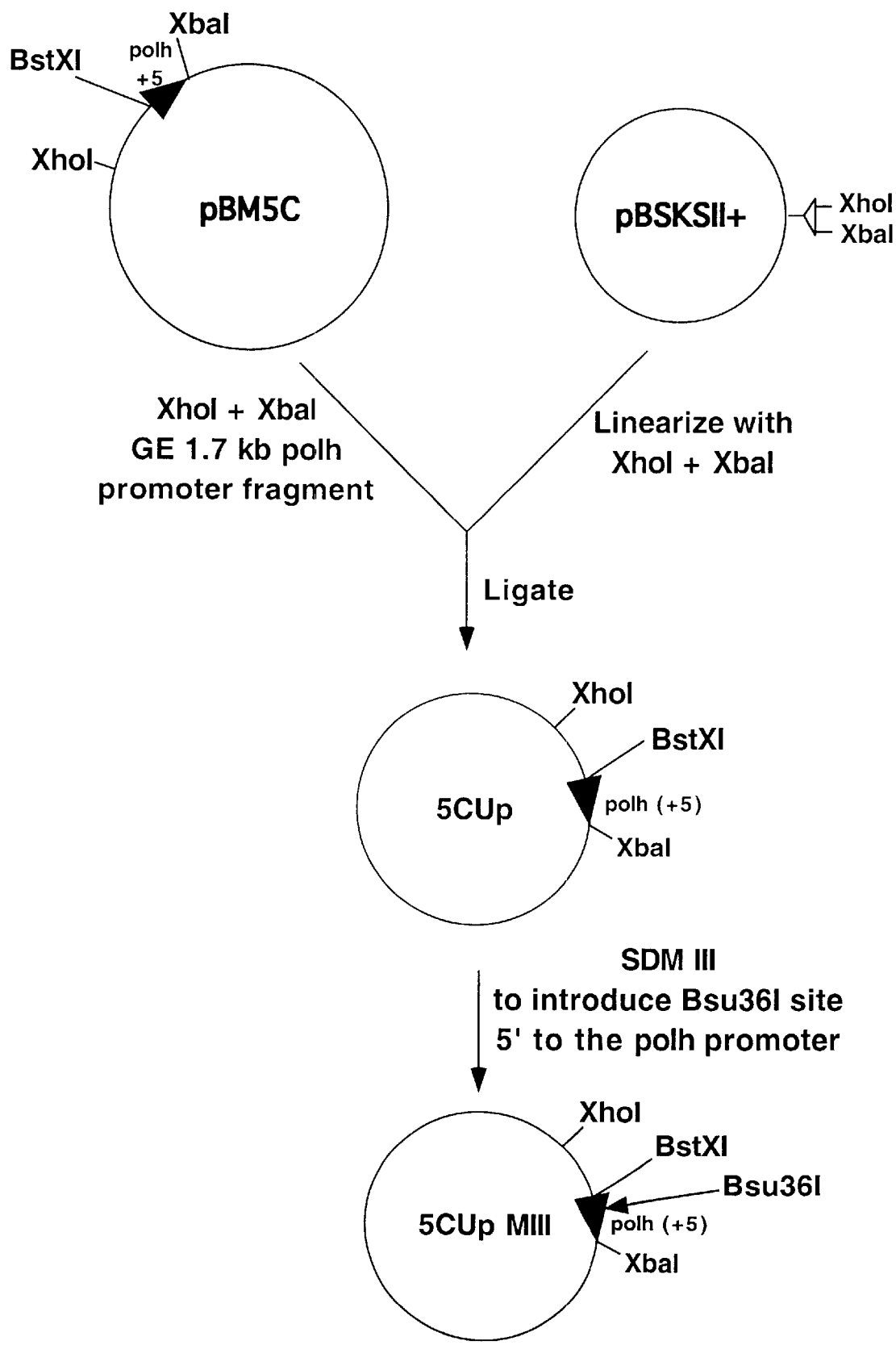

In order to introduce a Bsu36I restriction site in the polyhedrin upstream region, the polyhedrin promoter-containing XhoI+XbaI fragment was subcloned from the BmNPV transfer vector pBm5C into pBluescriptII cut with the same sites. This construct was called 5CUp (FIG. 2F).

A third round of SDM was carried out on 5CUp plasmid to introduce the Bsu36I restriction site within the polyhedrin promoter upstream region. This construct was called 5CUp-MIII (FIG. 2F), mutagenesis was confirmed by sequencing. The sequence of the oligonucleotide used to introduce the Bsu36I site (underlined) was 5' GTTTT TTATT AA CCTCAGG ATATC AAATG GAAAT AATAA CC 3' (SEQ ID NO:8) (the 3' end of the oligo represents the −66 nucleotide position with respect to the ATG start codon of the polyhedrin gene being +1). The nucleotide insertions are shown in bold. There is no reported ORF in this region.

Figure 2G:
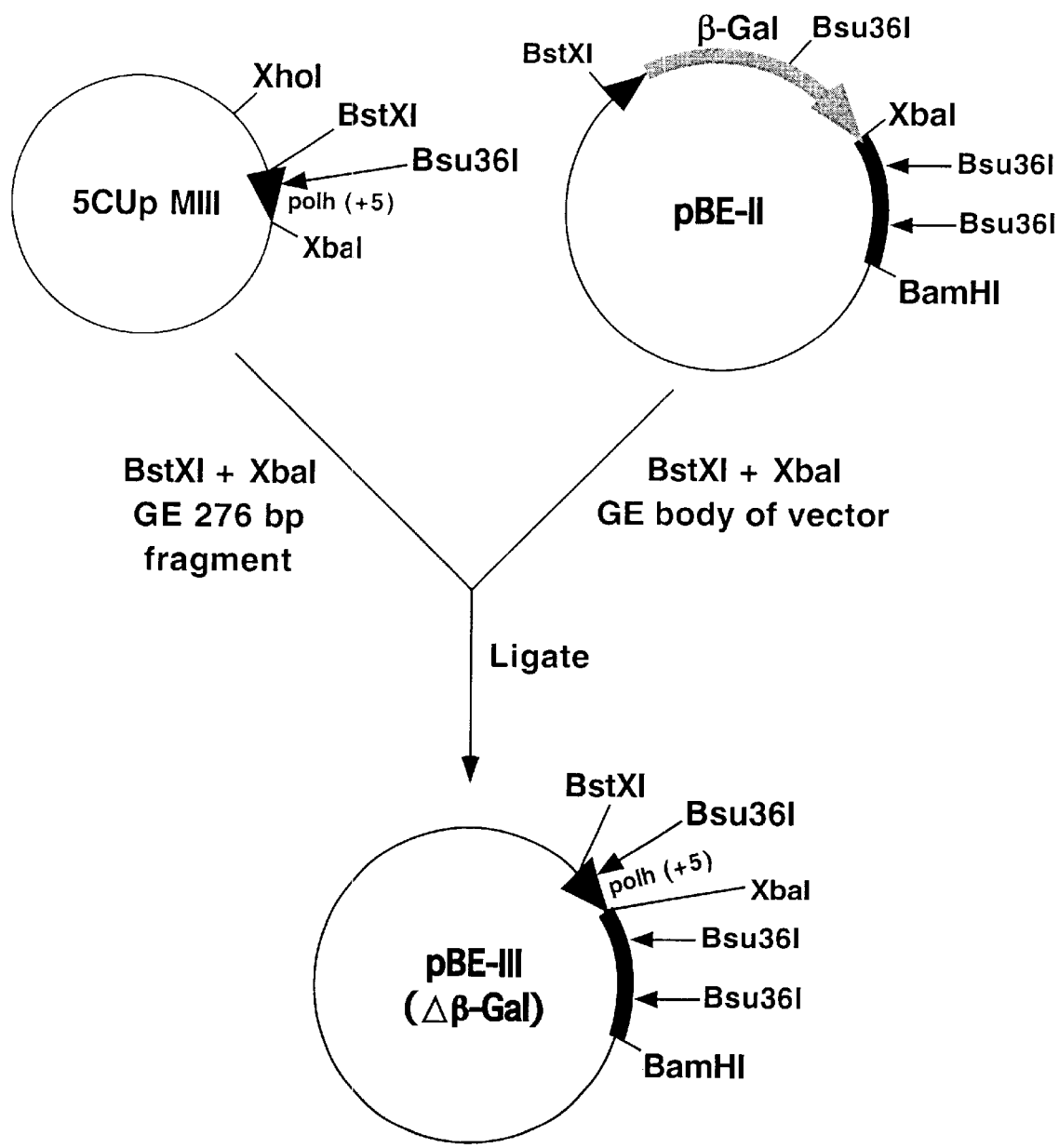

The three Bsu36I restriction sites were brought together by deleting the β-Gal gene from pBEII with BstXI+XbaI digestion and replacing the deletion with the 276 bp polyhedrin promoter bearing BstXI+XbaI fragment from 5CUp-MIII. The resultant construct was called pBEIII(δβ-Gal) (FIG. 2G).

Figure 2H:
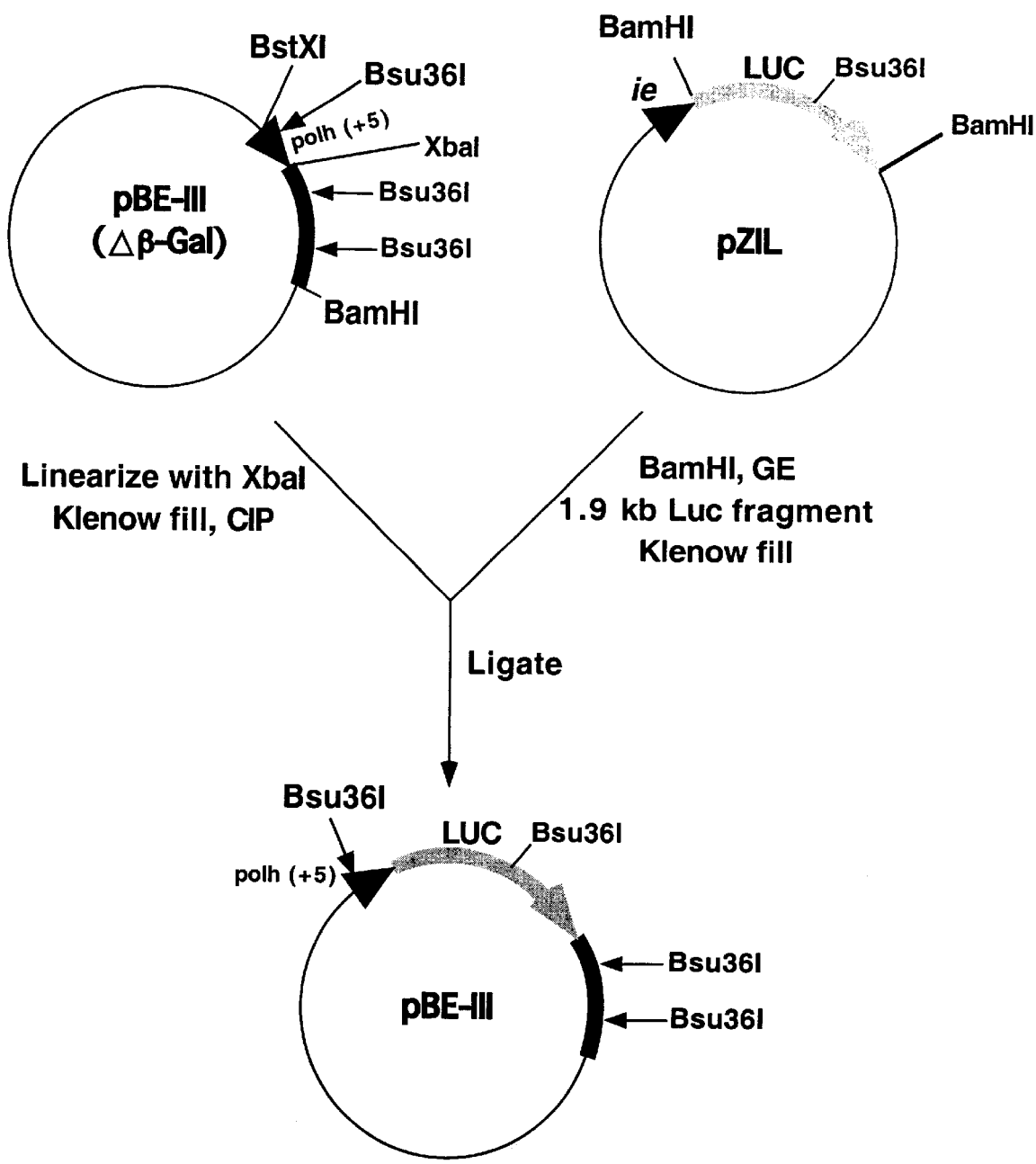

In the final step, the luciferase reporter gene was isolated as a 1.9 kb BamHI fragment from pZIL (Palhan et al., 1995, supra) and inserted into the Klenow filled XbaI site of BEIII(δβ-Gal) to generate pBEIII (FIG. 2H).

Constructing vBmBEIII. The BmNPV genomic sequence (Accession No. L33180) (SEQ ID NO:9) described in Gomi et al., Current Science 1996; 70: 147–153, which is incorporated herein by reference, was scanned against a database of restriction endonuclease sites (using MACVECTOR software) and Bsu36I was identified as one of the enzymes which did not cut the 130 kb circular viral DNA. Several potential sites within the polyhedrin gene upstream and downstream sequences were identified wherein Bsu36I restriction sites could be introduced by site directed mutagenesis. Sites were selected such that minimal changes to the DNA sequence at the wobble codon position would introduce the Bsu36I site without disturbing the amino acid coding sequence of the encoded protein (silent mutations).

Results

Construction of viruses with an essential segment flanked by multiple Bsu36I Sites. Viruses that had incorporated the β-Gal marker gene and the flanking Bsu36I sites from pBEI and pBEII were isolated from the products of recombination between the transfer vector and wildtype BmNPV-BGL viral DNA. The corresponding viruses, vBmBEI and vBmBEII were purified as blue plaques after β-Gal staining (King et al., The Baculovirus Expression System: A Laboratory Guide. Chapman & Hall, New York.). Viral DNA was isolated from pure occlusion negative viruses(Occ⁻) vBm-BEI (with two Bsu36I sites) and vBmBEII (with three Bsu36I sites) stocks and digested with Bsu36I. To check if all the viral DNA molecules were cut, a mock transfection was carried out with the digested viral DNAs. If the enzyme digestion was complete, none of the digested viral molecules could have given rise to viable viruses, hence no β-Gal expression. On the other hand, even if a few circular viral DNA molecules escaped digestion they would transfect BmN cells efficiently, be viable, and give rise to high levels of β-Gal expression. Surprisingly, high levels of β-Gal expression were seen from both vBmBEI- and vBmBEII-Bsu36I digests indicating that the enzyme digestions were not complete. The incomplete digestion was the result of the fastidious nature of Bsu36I which recognizes 7 bp restriction sites hidden in a large 130 kp viral genome. In order to overcome this problem a fourth Bsu36I site was introduced into viral DNA to facilitate 100% digestion of the viral DNA molecules thereby ensuring zero background of parental (non-recombined) viruses.

Figure 3:
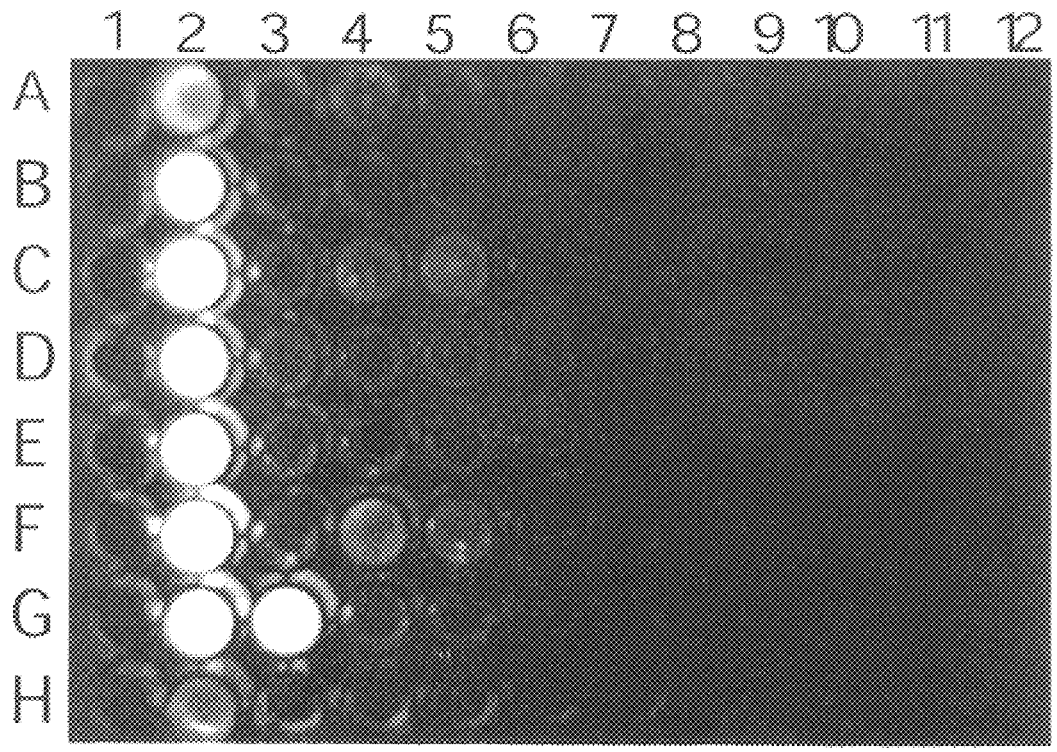
FIG. 3. Photograph of the 96 well LUC assay used in the primary screening for recombinant vBmBEIII virus.

Towards this goal, vBmBEIII (third generation of the Bombyx Easy system) was constructed by co-transfecting the pBEIII transfer vector DNA along with wildtype BmNPV-BGL viral DNA and selecting for Occ⁻ plaques which were further purified by 96-well LUC assay screening (FIG. 3). The supernatant from wells F2 (1°P6, primary round plaque #6) and G3 were selected for the final purification of vBmBEIII by a second round of plaque assay.

Figure 4A:
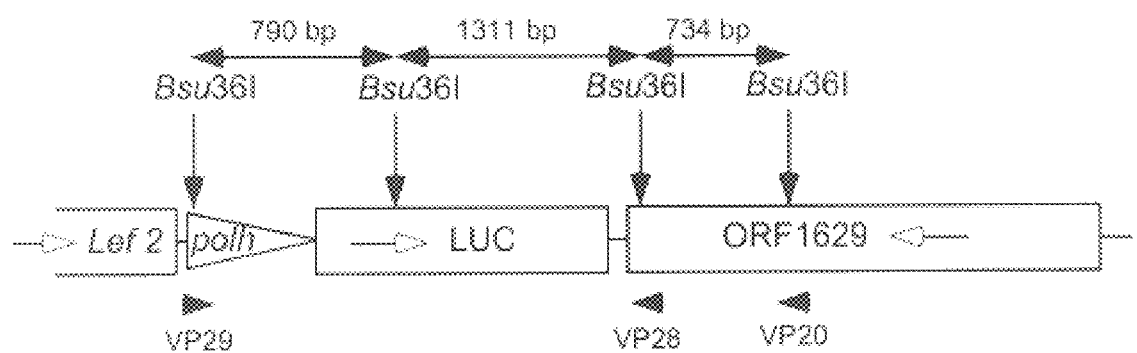
FIG. 4. Map of the vBmBEIII polyhedrin locus. "Luc" is luciferase, "polh" is the polyhedrin promoter; VP29, VP28, and VP20 are PCR primers specific for segments that contain the engineered Bsu36I restriction sites.
Figures 4B, 4C:
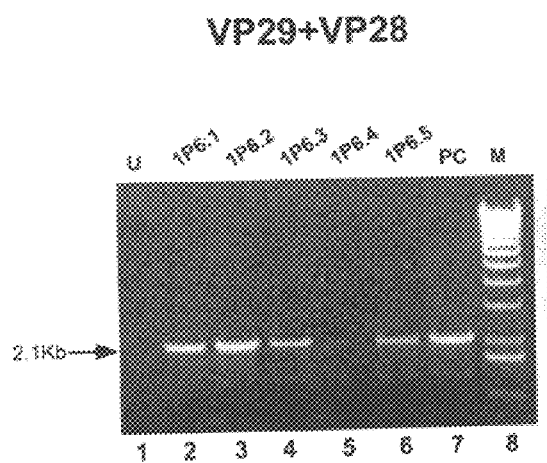
Figure 5A:
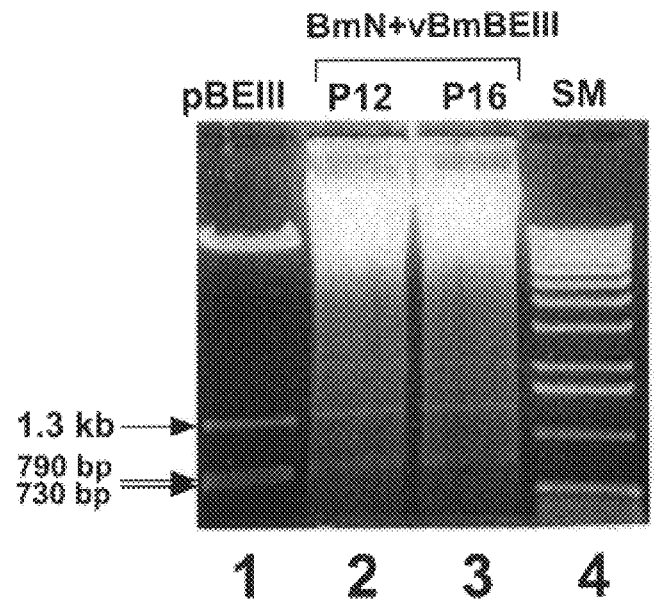
FIGS. 5A and 5B. PCR analysis confirmation of the vBmBEIII construction. (A) Amplification using primers VP29 and VP28 (see, FIG. 4). (B) Amplification using primers VP29 and VP20.
Figure 5B:
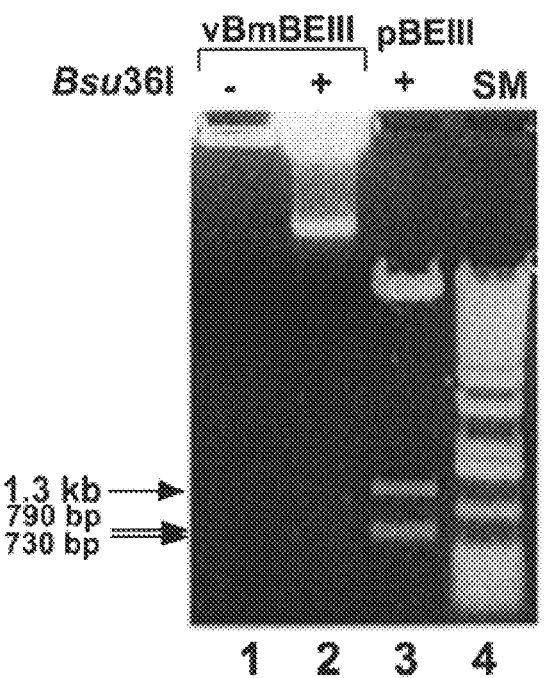

Purity, identity and presence of the four Bsu36I sites in vBmBEIII was confirmed by PCR and restriction analysis. A schematic representation of the polyhedrin locus of vBmBEIII is shown in FIG. 4A and as seen in FIGS. 4B and 4C all the five secondary plaques (derived from primary plaque #6) gave the expected size (2.1 kb with primers VP29+28, FIG. 4B) and (2.8 kb with primers VP29+20). PCR products similar to that obtained from pBEIII DNA taken as positive control. It should be noted that all of these primers that were used to introduce the mutations were the same, hence they will only anneal and prime synthesis if the Bsu36I sites are present. Bsu36I restriction digestion of total DNA from BmN cells infected with two different plaque isolates (P12 and P16) of vBmBEIII also confirmed the presence of all the four Bsu36I sites and gave the 1.3 kb, 790 bp, 730 bp fragments as seen from the PBEIII DNA digested with Bsu36I (FIG. 5A). Purified viral DNA when digested with Bsu36I also gave the same size bands at a much lower intensity as the amount of viral DNA was limiting (FIG. 5B).

EXAMPLE 2

Recombinant Protein Expression from vBmNPV

Materials and Methods

This example demonstrates that the Bombyx Easy BEVS provides a highly efficient system for expressing recombinant proteins. The Bombyx Easy BEVS system was used to generate a vBmfTIP30 recombinant baculovirus expression vector for expressing FLAG epitope-tagged TIP30 (an HIV interacting protein isolated from Hela cells).

Recombinant proteins. Uninfected or vBmf-TIP30 infected BmN cells ($10^7$) were washed with ice cold phosphate buffered saline (PBS) and sonicated in BC 500 buffer with 0.2% NP-40 and clarified as mentioned above for the fat bodies extract (FBE). FLAG-tagged TIP30 was purified from BmN cells whole cell extract (WCE) and B. mori FBE by single-step affinity chromatography over M2-Agarose resin per the manufacturer's instructions (Sigma). The beads were washed with BC500 buffer with 0.2% NP-40 before eluting with BC100 buffer containing 0.2 mg/μl FLAG peptide (DYKDDDDK). As positive control f-TIP30 was also purified from Sf21 cells infected with vAcf-TIP30 (Xiao et al., 2000, supra). Wildtype TAT were purified as a His-tagged fusion from E. coli under denaturing conditions and renatured by step dialysis (Xiao et al., 2000, supra), GST-CTD and GAL4-VP16 were also expressed and purified from E. coli (Xiao et al., 2000 supra). Western blot analysis was carried out by separating protein samples on a 10% SDS-PAGE gel and transferred to nitrocellulose membrane using a semi-dry Trans-Blot apparatus (Biorad). The membrane was blocked with 5% non-fat dry milk (NFDM) dissolved in TBST (50 mM tris-HCl pH 7.5, 150 mM sodium chloride and 0.1% tween 20) and probed with rabbit polyclonal anti-TIP30 antibodies (1:1000 dilution in TBST with 2.5% NFDM) followed by anti-rabbit IgG-HRPO conjugate (1:3000 dilution in TBST) and developed using the ECL kit (Amersham).

Functional activity of recombinant f-TIP30 by an in vitro kinase assay. Briefly, the in-vitro kinase assay was carried out by incubating 5 ng of recombinant f-TIP30 with 100 ng of GST-CTD and 5 mCi of [g-$^{32}$P]ATP (3000 Ci/mmol) in casein kinase II buffer at 30° C. for 30 mins. The reaction was stopped by adding SDS-PAGE gel loading buffer and the samples were separated on a 10% SDS-PAGE gel. Bands were visualized by Gel code Blue (Pierce) Coomassie blue staining before drying and autoradiography.

Results

Figure 6:
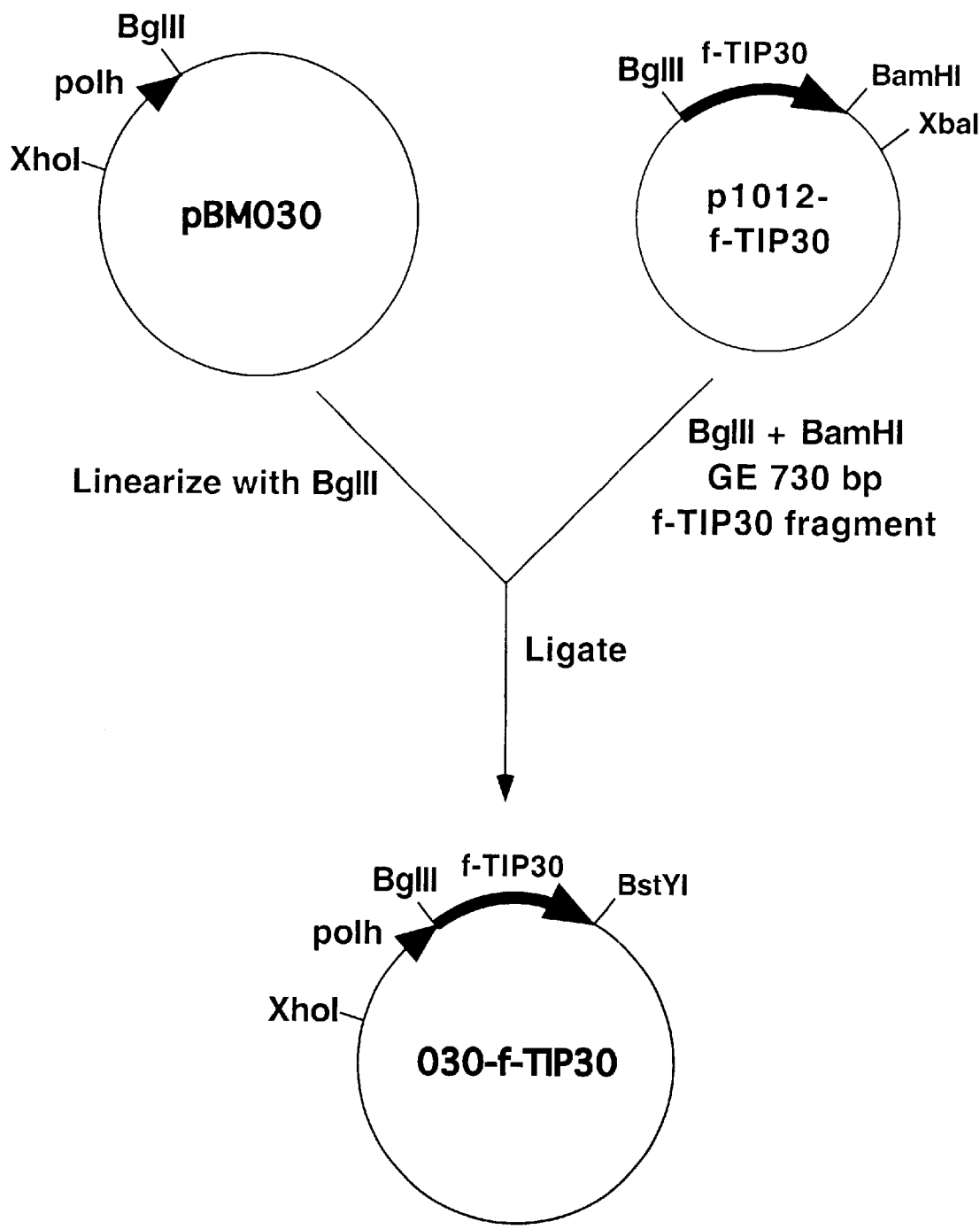
FIG. 6. Schematic figure showing the subcloning of f-TIP30 into the pBM030 transfer vector.
Figure 7:
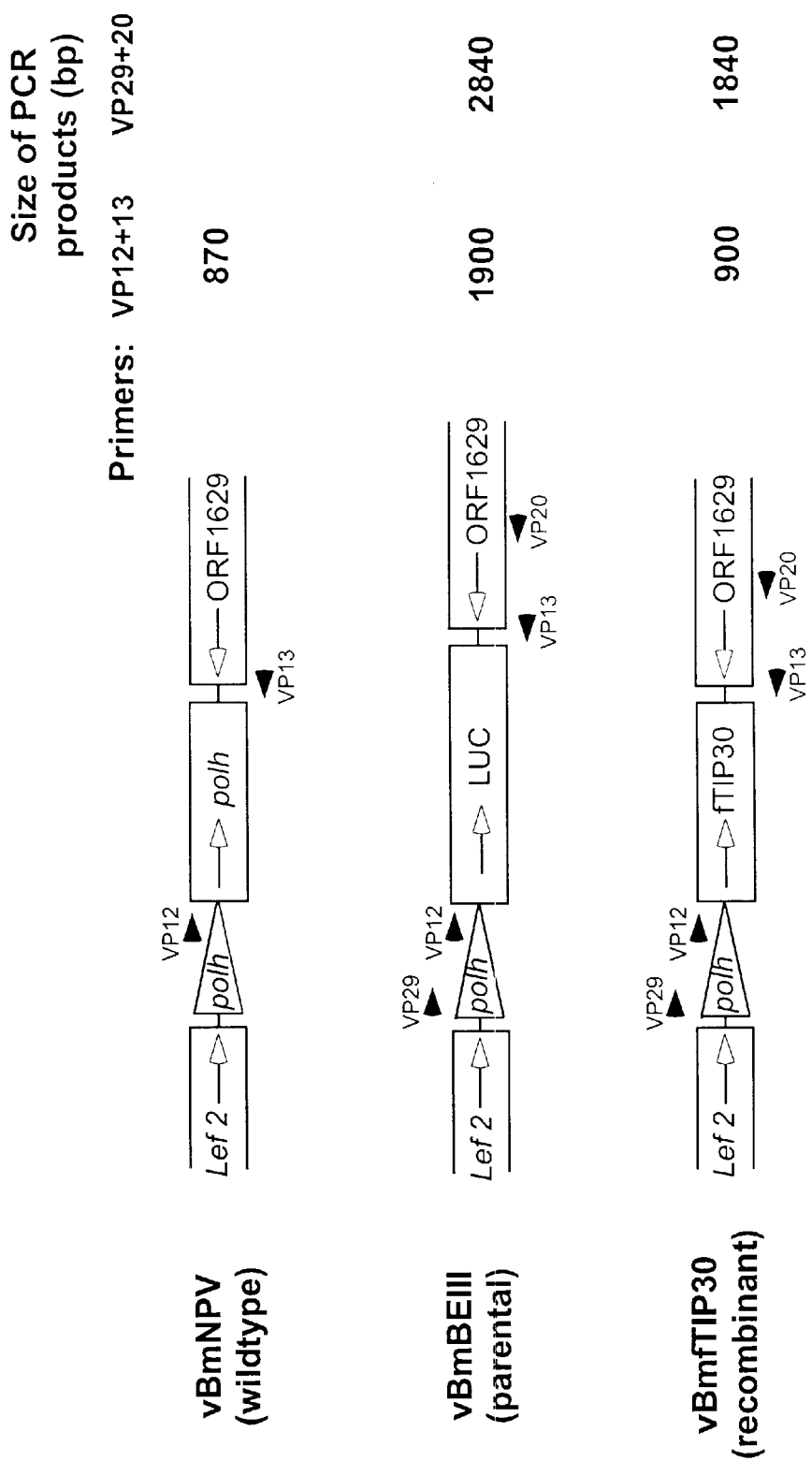
FIG. 7. Schematic figure showing the polyhedrin locus in three viruses: wildtype vBmNPV, parental vBmBEIII and recombinant vBmf-TIP30 together with the expected PCR product sizes. The position and orientation of the Lef2, polh/LUC/f-TIP30 and ORF1629 genes is indicated by the empty arrows. The position of the forward (VP12 and VP29) and reverse (VP13 and VP20) PCR primers are indicated by filled arrowheads.
Figure 8A:
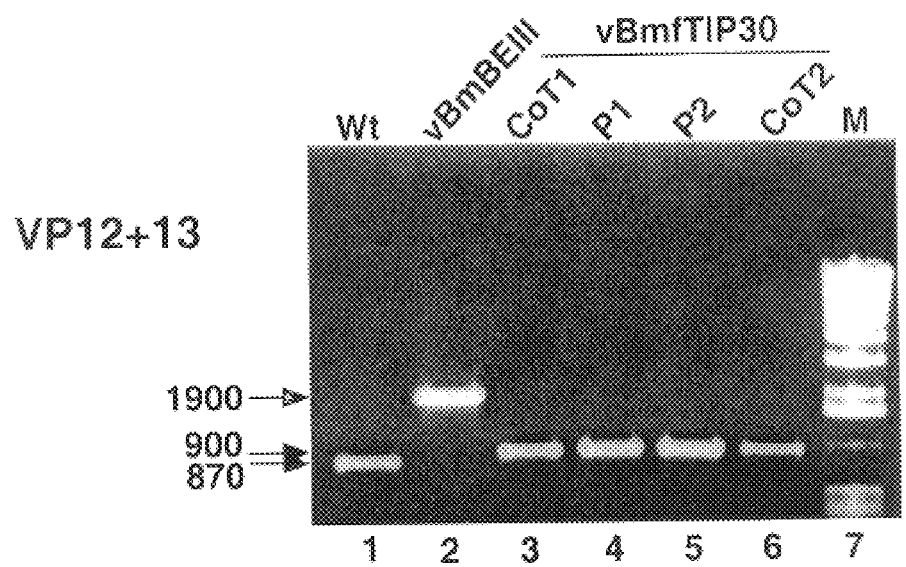
FIGS. 8A and B. PCR analysis of recombinant virus purity for the two different co-transfections (CoT1 and CoT2) and from two consecutively amplified passages (P1 and P2) of virus stocks. PCR analysis was achieved using primer sets VP12+13 (B) or VP29+20 (C) and the products were analyzed on a 0.8% agarose gel along with a 1 kb DNA ladder (M).
Figure 8B:
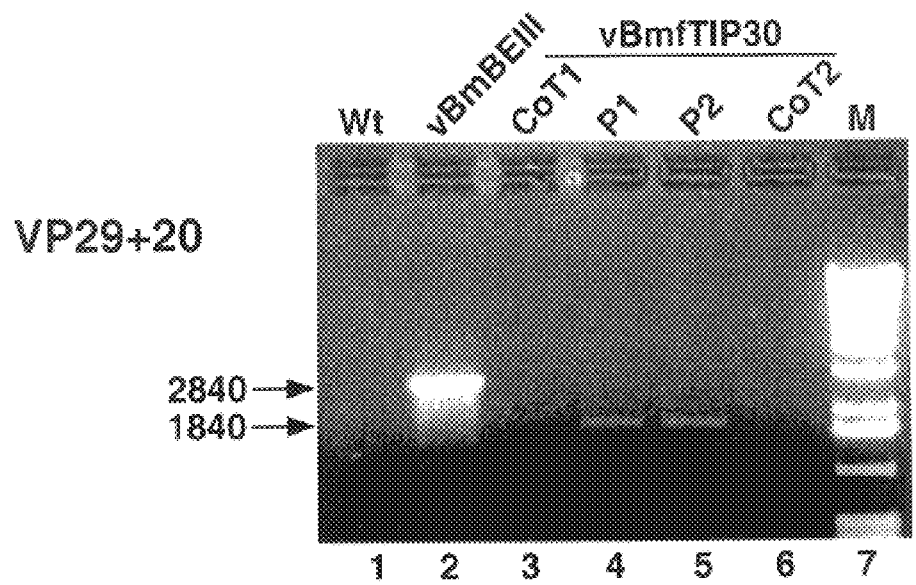

Efficient generation of recombinant vBmf-TIP30. The utility of Bsu36I-digested vBmBEIII viral DNA to rapidly and efficiently generate recombinant BmNPV vectors was demonstrated by co-transfecting Bsu36I-digested vBmBEIII viral DNA along with the 030-f-TIP30 transfer vector bearing the FLAG epitope tagged TIP30 gene under the control of the polyhedrin promoter. The f-TIP30 cDNA was first subcloned into the pFLAG7-sense vector from the pRSET vector, it was later excised along with the FLAG-tag and subcloned into the pBM030 transfer vector (FIG. 6). No plaque assay was necessary to purify the recombinant virus. The purity and identity of the recombinant vBmf-TIP30 virus was confirmed by PCR. FIG. 7 shows a schematic representation of the polyhedrin locus of three viruses—wildtype vBmNPV, parental vBmBEIII and recombinant vBmf-TIP30 along with the expected PCR product sizes with the two different primer pairs (VP12 and VP13 and VP29 and VP20). PCR analysis with both the primer pairs (FIGS. 8B and 7C) showed 100% recombinant virus purity for the two different co-transfections (CoT1 and CoT2) and from two consecutively amplified passages (P1 and P2) virus stocks. However, the higher size parental (vBmBEIII specific) bands were not seen in any of the recombinant virus stocks with either primer pairs even after two rounds of amplification. This highly sensitive analysis confirmed that recombinant virus vectors are generated rapidly with 100% efficiency using the Bombyx Easy III system.

Figures 9, 11:
FIG. 9. Western blot analysis using rabbit polyclonal anti-TIP30 antibodies to confirm the identity and expression of recombinant f-TIP30 expressed in BmN cells infected with vBmf-TIP30. Total cellular lysates from uninfected (U) BmN cells, or those infected with either Co-transfection (CoT) supernatant or passage 1 (P1) amplified stock of vBmf-TIP30 along with recombinant f-TIP30 purified from Sf21 cells infected with vAcf-TIP30 as positive control (PC) were analyzed.
FIG. 11. Western blot analysis showing the functional activity of recombinant f-TIP30 confirmed by an in vitro kinase assay. Recombinant f-TIP30 (purified from silkworm larvae) was incubated either alone (lane 1) or with GST-CTD (lane 3–6).

Authenticity of recombinant f-TIP30 purifed from BmN cells. Western blot analysis using rabbit polyclonal antisera against f-TIP30 protein confirmed the authenticity of recombinant f-TIP30 expressed in BmN cells (FIG. 9). The expression level was high enough to be detectable at the co-transfection stage (lane 2) itself and the signal improved as the virus titer increased during passage 1 (P1) amplification of the virus stock (lane 3).

Purification of recombinant f-TIP30 from BmN cells and B. mori larvae. High levels of recombinant f-TIP30 were purified to near homogeneity by single step affinity chromatography over M2-agarose resin from BmN cells WCE and B. mori FBE (FIGS. 10A and B). No degradation and higher expression levels were seen in the larval fat bodies in comparison to the BmN cells. The yields of purified protein were quantitated in comparison to BSA standards and estimated to be approximately 3 mgs of purified f-TIP30 from FBE of 50 silkworm larvae. It should be noted that at least 30% of the expressed protein appears to be still remaining in the M2-agarose unbound fraction (FIG. 10B, lane 6) which could be purified using fresh M2-agarose resin. The beads used in the first round of purification could have been saturated by the large excess amount of recombinant protein present in the B. mori FBE.

Functional Assay with Recombinant f-TIP30. Recombinant FLAG-tagged TIP30 was purified from silkworm larvae and its biological activity was demonstrated by showing that it could phosphorylate the carboxy terminal domain (CTD) of RNA polymerase II fused to GST (GST-CTD) in an in vitro kinase assay (FIG. 11, lane 3). Furthermore, the HIV TAT trans-activating protein was found to stimulate the kinase activity of recombinant f-TIP30 on GST-CTD substrate in a dose dependant manner (FIG. 11, lanes 4–6). As a negative control, even the maximum amount of TAT by itself showed no phosphorylation of GST-CTD (lane 2). In order to investigate whether TAT had any stimulatory effect on the kinase activity of f-TIP30, limiting amounts of recombinant enzyme were used in this trans-phosphorylation assay. Hence, f-TIP30 did not show any auto-phosphorylation (lane 1).

Discussion

Employment of the Bombyx Easy system resulted in high yields of recombinant proteins made economically in silkworm larvae coupled with the high efficiency of rapidly generating recombinant baculoviruses which makes the BmNPV-silkworm larvae based expression system an attractive alternative to the conventional *Autographa californica* nuclear polyhedosis virus (AcNPV)-Sf9 cells based baculovirus expression system.

The results also exemplify the value of a system that can generate recombinant baculovirus expression vectors at 100% frequencies to reduce the time taken to isolate recombinant baculoviruses, thereby facilitating studies that involve the expression of large numbers of variant proteins and encourage researchers and biotechnology/pharmaceutical industry to try this excellent economical silkworm larval expression system.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A recombinant *Bombyx mori* nuclear polyhedrosis virus (BmNPV), which BmNPV has a genome comprising a restriction endonuclease site in a polyhedrin promoter region and a second restriction endonuclease site in an essential gene region located downstream of the polyhedrin promoter region, wherein the restriction endonuclease sites are not found outside of the segment of the genome delineated by the restriction endonuclease sites in the polyhedrin promoter region at the upstream end and the essential gene region in the downstream end, and wherein cutting of the genome by a restriction enzyme specific for the restriction site in the essential gene knocks out function of the essential gene.

2. The recombinant BmNPV of claim 1, which further comprises a second restriction endonuclease site in the essential gene.

3. The recombinant BmNPV of claim 1, which further comprises a reporter gene operably associated with the polyhedrin promoter.

4. The recombinant BmNPV of claim 2, which further comprises a reporter gene operably associated with the polyhedrin promoter.

5. The recombinant BmNPV of claim 4, wherein the reporter gene contains a restriction endonuclease recognition site.

6. The recombinant BmNPV of claim 1, wherein each restriction endonuclease site is the same.

7. The recombinant BmNPV of claim 6, wherein the restriction endonuclease sites are not found in wildtype BmNPV.

8. The recombinant BmNPV of claim 7, wherein the restriction endonuclease sites are Bsu36I restriction endonuclease sites.

9. The recombinant BmNPV of claim 1, wherein the essential gene is ORF 1629.

10. The recombinant BmNPV of claim 2, wherein the essential gene is ORF 1629, and restriction cleavage of the second restriction site deletes at least 30% of a C-terminal portion of a protein encoded by ORF 1629.

11. The recombinant BmNPV of claim 3, wherein the reporter gene is luciferase.

12. A linear BmNPV, which BmNPV has one end comprising a cut restriction endonuclease site in a polyhedrin promoter region and a second end comprising a second cut in a restriction endonuclease site in an essential gene region, wherein the essential gene is located downstream of the polyhedrin promoter region in an intact BmNPV genome.

13. The linear BmNPV of claim 12, wherein the essential gene is ORF 1629.

14. The linear BmNPV of claim 13, wherein the cut results in deletion of a major portion of the C-terminus of the protein encoded by ORF 1629.

15. A method for preparing a recombinant *Bombyx mori* nuclear polyhedrosis virus (BmNPV), which BmNPV has a genome comprising a restriction endonuclease site in a polyhedrin promoter region and a second restriction endonuclease site in an essential gene region located downstream of the polyhedrin promoter region, which method comprises:

(a) introducing a restriction site into the polyhedrin promoter;

(b) introducing a restriction site into the essential gene; and (c) selecting recombinant BmNPV that contain both restriction sites.

16. The method according to claim 15, further comprising introducing a second restriction site into the essential gene.

17. The method according to claim 15, further comprising introducing a reporter gene into the BmNPV genome, wherein the reporter gene is operatively associated with the polyhedrin promoter and has a single site for the same restriction endonuclease as that whose sites are introduced in the BmNPV polyhedrin locus.

18. A transfer vector comprising a region of an BmNPV genome containing or upstream of a polyhedrin promoter, a cassette insertion site operably associated with the polyhedrin promoter or another promoter effective in silkworm cells, and a region of a BmNPV genome containing an essential gene, wherein the essential gene is located downstream of the polyhedrin promoter in a wildtype BmNPV genome and is oriented in the transfer vector the same way relative to the polyhedrin promoter as it is in wildtype BmNPV, and wherein the two regions are of sufficient size to permit homologous recombination with a BmNPV vector.

19. The transfer vector of claim 18, wherein the essential gene is ORF 1629.

20. The transfer vector of claim 18, further comprising a gene of interest inserted into the cassette insertion site.

21. The transfer vector of claim 20, wherein the gene of interest encodes for a HIV Tat interacting protein (f-TIP30).

22. A *Bombyx mori* (silkworm) cell transfected with the BmNPV of claim 1.

23. The *B. mori* cell of claim 22 transfected with a transfer vector comprising a region of an BmNPV genome containing or upstream of a polyhedrin promoter, a cassette insertion site operably associated with the polyhedrin promoter or another promoter effective in silkworm cells, and a region of a BmNPV genome containing an essential gene, wherein:

(a) the essential gene is located downstream of the polyhedrin promoter in a wildtype BmNPV genome and is oriented in the transfer vector the same way relative to the polyhedrin promoter as it is in wildtype BmNPV;

(b) the two regions are of sufficient size to permit homologous recombination with a BmNPV vector; and (c) a gene of interest is inserted into the cassette insertion site.

24. The *B. mori* cell of claim 23, wherein the gene of interest encodes for a HIV Tat interacting protein (f-TIP30).

25. The *B. mori* cell of claim 23 which is a BmN cell in tissue culture.

26. The *B. mori* cell of claim 23 which is in a silkworm larva.

27. A method for producing a protein encoded by a gene of interest, which method comprises isolating the protein expressed by the BmN cell of claim 24 cultured under conditions that permit expression of the protein encoded by the gene of interest.

28. The method according to claim 27, wherein the gene of interest encodes for a HIV Tat interacting protein (f-TIP30).

29. A method for producing a protein encoded by a gene of interest, which method comprises isolating the protein expressed by the silkworm larva of claim 26 reared under conditions that permit expression of the protein encoded by the gene of interest.

30. The method according to claim 29, wherein the protein is isolated from fat body extracts.

31. The method according to claim 29, wherein the expressed protein includes a secretory signal and is isolated from interstitial fluid.

32. The method according to claim 29, wherein the expressed protein includes a HIV Tat interacting protein (f-TIP30).

* * * * *

SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: VP12 Forward Primer

```
<400> SEQUENCE: 1
ataaccatct cgcaaataaa taag                                              24

<210> SEQ ID NO 2
<211> LENGTH: 41
<212> TYPE: DNA
<213> ORGANISM: Artificial Sequence
<220> FEATURE:
<223> OTHER INFORMATION: VP29 Forward Primer

<400> SEQUENCE: 2 gtttttatt aacctcagga tatcaaatgg aaataataac c                            41

<210> SEQ ID NO 3
<211> LENGTH: 23
<212> TYPE: DNA
<213> ORGANISM: Artificial Sequence
<220> FEATURE:
<223> OTHER INFORMATION: VP13 Reverse Primer

<400> SEQUENCE: 3
aattgtctgt aaatcaacaa cgc                                               23

<210> SEQ ID NO 4
<211> LENGTH: 22
<212> TYPE: DNA
<213> ORGANISM: Artificial Sequence
<220> FEATURE:
<223> OTHER INFORMATION: VP20 Reverse Primer

<400> SEQUENCE: 4
gccgacgact gtgttgccta ag                                                22

<210> SEQ ID NO 5
<211> LENGTH: 30
<212> TYPE: DNA
<213> ORGANISM: Artificial Sequence
<220> FEATURE:
<223> OTHER INFORMATION: VP28 Reverse Primer

<400> SEQUENCE: 5
cattaaattt gtaatcctta gggtggtatg                                        30

<210> SEQ ID NO 6
<211> LENGTH: 23
<212> TYPE: DNA
<213> ORGANISM: Artificial Sequence
<220> FEATURE:
<223> OTHER INFORMATION: Synthesized oligonucleotide

<400> SEQUENCE: 6
gtgttgccta aggagcccaa acg                                               23

<210> SEQ ID NO 7
<211> LENGTH: 30
<212> TYPE: DNA
<213> ORGANISM: Artificial Sequence
<220> FEATURE:
<223> OTHER INFORMATION: Synthesized oligonucleotide

<400> SEQUENCE: 7
cataccaccc taaggattac aaatttaatg                                        30

<210> SEQ ID NO 8
```

```
<211> LENGTH: 41
<212> TYPE: DNA
<213> ORGANISM: Artificial Sequence
<220> FEATURE:
<223> OTHER INFORMATION: Synthesized oligonucleotide

<400> SEQUENCE: 8 gtttttatt aacctcagga tatcaaatgg aaataataac c                    41

<210> SEQ ID NO 9
<211> LENGTH: 1592
<212> TYPE: DNA
<213> ORGANISM: Bombyx mori nuclear polyhedrosis virus

<400> SEQUENCE: 9
atgccgaatt attcatacac ccccaccatc gggcgtactt acgtgtacga caataaatat    60
tacaaaaact tgggctgtct tatcaaaaac gccaagcgca agaagcacct agtcgaacat   120
gaacaagagg agaagcaatg ggatcttcta gacaactaca tggttgccga agatcccttt   180
ttaggaccgg gcaaaaacca aaaacttacc ctttttaaag aaattcgcag tgtgaaaccc   240
gataccatga agttaatcgt caactggagc ggcaaagagt ttttgcgtga aacttggacc   300
cgttttgttg aggacagctt ccccattgta aacgaccaag aggtgatgga cgtgtacctc   360
gtcgccaacc tcaaacccac acgccccaac aggtgctaca agttcctcgc tcaacacgct   420
cttaggtggg aagaagacta cgtgccccac gaagtaatca gaattgtgga gccatcctac   480
gtgggcatga acaacgaata cagaattagt ctggctaaaa agggcggcgg ctgcccaatc   540
atgaacatcc acagcgagta caccaactcg ttcgagtcgt tgtgaaccg cgtcatatgg    600 gagaacttct acaaacccat cgtttacatc ggcacagact ctgccgaaga agaggaaatc   660
ctaattgagg tttctctcgt tttcaaaata aaggagtttg caccagacgc gcctctgttc   720
actggtccgg cgtattaaaa cactatacat tgttattagt acatttatta agcgttagat   780
tctgtgcgtt gttgatttac agacaattgt tgtacgtatt ttaataattc attaaatttg   840
taatctttag ggtggtatgt tagagcgaaa atcaaatgat tttcagcgtc tttgtatctg   900
aatttaaata ttaaatcctc aatagatttg taaaataggt ttcgattggt ttcaaacaag   960
ggttgttttt gcaaaccgat ggctggacta tctaatggat tttcgctcaa caccacacga  1020
cttgccaaat cttgtagcag caatctagct ttgtcgatat tcgtttgtgt tttgttttgt  1080
aataaagatt cgacgtcgtt caaaatatta tgcgcttttg tattttttc atcactgtcg   1140 ttggtgtaca attgactcga cgtaaacacg ttaaataaag cttggacata tttaacatcg  1200
ggcgcgttag gccgattatt gccgccgtcg tcccaaccct cgtcgttaga agttgcttcc  1260
gaagacgatt tgccatagc cacacgacgc ctattaattg tgtcgactaa cacgtccgcg   1320
atcaaatttt tagttgttga gttttcgga attatttctg attgcggacg tttttgtgcg  1380
ggtttcaatc taactgtgcc cgattttaat tcagacaaca cgttagaaag cgatggtgca  1440
ggcggtggta acatttcagc cggcaaatct actaatggcg gctgtaatgg agctgatgat  1500
aaatctatca ttggtggagg cgcaggcggg gctggcggcg gaggtggtgg cggcggtgat  1560
gcagacggcg gtttgggctc tttaggcaac ac                              1592
```